(12) United States Patent
Edwards et al.

(10) Patent No.: US 11,246,756 B2
(45) Date of Patent: Feb. 15, 2022

(54) HEALTHCARE TEXTILES

(71) Applicants: The United States of America, as Represented by the Secretary of Agriculture, Washington, DC (US); H&H Medical Inc., Bena, VA (US); TJ Beall, Greenwood, MS (US)

(72) Inventors: Judson V. Edwards, Mandeville, LA (US); Joseph Dacorta, Bena, VA (US); Gary Lawson, Greenwood, MS (US)

(73) Assignees: The United States of America, as represented by the Secretary of Agriculture, Washington, DC (US); H & H Medical Corporation, Williamsburg, VA (US); T.J. Beall Company, Greenwood, MS (US)

( * ) Notice: Subject to any disclaimer, the term of this patent is extended or adjusted under 35 U.S.C. 154(b) by 503 days.

(21) Appl. No.: 16/110,169

(22) Filed: Aug. 23, 2018

(65) Prior Publication Data

US 2019/0380878 A1 Dec. 19, 2019

Related U.S. Application Data

(60) Provisional application No. 62/549,676, filed on Aug. 24, 2017.

(51) Int. Cl.
*A61F 13/00* (2006.01)
*A61L 15/28* (2006.01)
(Continued)

(52) U.S. Cl.
CPC .. *A61F 13/00012* (2013.01); *A61F 13/51113* (2013.01); *A61F 13/51121* (2013.01);
(Continued)

(58) Field of Classification Search
None
See application file for complete search history.

(56) References Cited

U.S. PATENT DOCUMENTS

| | | |
|---|---|---|
| 6,809,231 B2 | 10/2004 | Edwards |
| 9,463,119 B2 | 10/2016 | Robertsson et al. |

(Continued)

FOREIGN PATENT DOCUMENTS

| | | |
|---|---|---|
| JP | 2000175958 A | 6/2000 |
| WO | 2015041862 A1 | 3/2015 |

OTHER PUBLICATIONS

Edwards et al. "Electrokinetic and Hemostatic Profiles of Nonwoven Cellulosic/Synthetic Fiber Blends with Unbleached Cotton", Functional Biomaterials, vol. 5, pp. 273-287, Nov. 28, 2014 (Year: 2014).*

(Continued)

*Primary Examiner* — Shawn Mckinnon
(74) *Attorney, Agent, or Firm* — John D. Fado; Maria Restrepo-Hartwig

(57) ABSTRACT

Single layered nonwoven wound dressings containing (1) about 5% by weight to about 95% by weight (e.g., 5% to 95%) non-scoured, non-bleached greige cotton fibers, (2) about 5% by weight to about 95% by weight (e.g., 5% to 95%) bleached cotton fibers, and (3) about 5% by weight to about 60% by weight (e.g., 5% to 60%) hydrophobic fibers (e.g., polypropylene, nylon); all percentages adding up to 100 wt %. Also, multi-layered nonwoven wound dressings, containing (1) at least one inner layer containing (a) about 50% by weight to about 95% by weight (e.g., 50% to 95) non-scoured, non-bleached greige cotton fibers and (b) about 5% by weight to about 50% by weight (e.g., 5% to 50%) hydrophobic fibers, all percentages adding up to 100 wt %, and (2) at least one outer layer containing (a) about 5% by weight to about 95% by weight (e.g., 5% to 95%)

(Continued)

non-scoured, non-bleached greige cotton fibers, (b) about 5% by weight to about 95% by weight (e.g., 5% to 95%) bleached cotton fibers, and (c) about 5% by weight to about 60% by weight (e.g., 5% to 60%) hydrophobic fibers (e.g., polypropylene, nylon); all percentages adding up to 100 wt %.

17 Claims, 11 Drawing Sheets
(8 of 11 Drawing Sheet(s) Filed in Color)

(51) Int. Cl.
*A61L 15/44* (2006.01)
*A61F 13/511* (2006.01)
*A61L 15/24* (2006.01)
*A61L 15/42* (2006.01)
*D04H 1/425* (2012.01)
*A61L 15/40* (2006.01)
*D04H 1/498* (2012.01)

(52) U.S. Cl.
CPC ............ *A61L 15/24* (2013.01); *A61L 15/28* (2013.01); *A61L 15/425* (2013.01); *A61L 15/44* (2013.01); *D04H 1/425* (2013.01); *A61F 2013/0054* (2013.01); *A61F 2013/00106* (2013.01); *A61F 2013/00217* (2013.01); *A61F 2013/00319* (2013.01); *A61F 2013/00736* (2013.01); *A61F 2013/00744* (2013.01); *A61F 2013/00748* (2013.01); *A61L 15/40* (2013.01); *D04H 1/498* (2013.01)

(56) References Cited

U.S. PATENT DOCUMENTS

2006/0275349 A1* 12/2006 Andrews ............ A61L 26/0066
424/443
2017/0156551 A1* 6/2017 Weinberg ................ A47K 7/03

OTHER PUBLICATIONS

Edwards, J. Vincent et al., "Electrokinetic and Hemostatic Profiles of Nonwoven Cellulosic/Synthetic Fiber Blends with Unbleached Cotton", J. Funct. Biomater, (2014), 5:273-287.
International Searching Authority, PCT/US2018/047869 for The United States of America, as Represented by the Secretary of Agriculture, International Filing date Aug. 24, 2018.
Edwards, JV et al., "Fluid handling and fabric handle profiles of hydroentangled greige cotton and spunbond polypropylene nonwoven topsheets," University of Leeds, Journal of Materials: Design and Applications (2015), 0(0);1-13.

* cited by examiner

HEALTHCARE TEXTILES

REFERENCE TO RELATED APPLICATION

This application claims the benefit of U.S. Provisional Application No. 62/549,676, filed 24 Aug. 2017, which is incorporated herein by reference in its entirety.

BACKGROUND OF THE INVENTION

Disclosed herein are single layered nonwoven wound dressings containing (1) about 5% by weight to about 95% by weight (e.g., 5% to 95%) non-scoured, non-bleached greige cotton fibers (preferably about 30% by weight to about 80% by weight (30-80), more preferably about 50% by weight to about 60% by weight (50-60)), (2) about 5% by weight to about 95% by weight (e.g., 5% to 95%) bleached cotton fibers (preferably about 20% by weight to about 70% by weight (20-70), more preferably about 20% by weight to about 30% by weight (20-30)), and (3) about 5% by weight to about 60% by weight (e.g., 5% to 60%) hydrophobic fibers (e.g., polypropylene, nylon) (preferably about 5% by weight to about 50% by weight (5-50), more preferably about 5% by weight to about 20% by weight (5-20)); all percentages adding up to 100 wt %. Also, multi-layered nonwoven wound dressings, containing (1) at least one inner layer containing (a) about 50% by weight to about 95% by weight (e.g., 50% to 95) non-scoured, non-bleached greige cotton fibers (preferably about 60% by weight to about 80% by weight (60-80); more preferably about 50% by weight to about 60% by weight (50-60)) and (b) about 5% by weight to about 50% by weight (e.g., 5% to 50%) hydrophobic fibers (preferably about 20% by weight to about 40% by weight (20-40), more preferably about 40% by weight to about 50% by weight (40-50)), all percentages adding up to 100 wt %, and (2) at least one outer layer containing (a) about 5% by weight to about 95% by weight (e.g., 5% to 95%) non-scoured, non-bleached greige cotton fibers (preferably about 30% by weight to about 80% by weight (30-80), more preferably about 50% by weight to about 60% by weight (50-60)), (b) about 5% by weight to about 95% by weight (e.g., 5% to 95%) bleached cotton fibers (preferably about 20% by weight to about 70% by weight (20-70), more preferably about 20% by weight to about 30% by weight (20-30)), and (c) about 5% by weight to about 60% by weight (e.g., 5% to 60%) hydrophobic fibers (e.g., polypropylene, nylon) (preferably about 5% by weight to about 50% by weight (5-50), more preferably about 5% by weight to about 20% by weight (5-20)); all percentages adding up to 100 wt %.

Half of all deaths on the battlefield are caused by uncontrolled hemorrhage (Bellamy, R. F., Military Medicine, 149: 55-62 (1984); Sauia, A., et al., Arch Surg., 129: 39-45 (1994)). In addition, high blood loss can lead to hypothermia, multiple organ failure, and infection (Cosgriff, N., et al., J. Trauma., 42: 857-862 (1997); Champion, H. R., et al., J. Trauma, 54: S13-S19 (2003)). Thus, rapid hemostasis is essential for survival and recovery. The development of improved hemostatic agents for use in lethal extremity arterial hemorrhages has increased over recent years. The U.S. Army Institute for Surgical Research (USISR) and the Uniformed Services University of the Health Sciences has outlined ideal properties needed in a battlefield dressing (Abou-Okeil, A., et al., Carbohydr. Polym., 90: 658-666 (2012)). These include the following properties: (1) being able to rapidly stop large vessel arterial and venous bleeding two minutes after application when applied to an actively bleeding wound through a pool of blood; (2) no requirement for mixing or preapplication preparation; (3) simplicity of application by wounded victim, buddy, or medic; (4) light weight and durable; (5) long shelf life in extreme environments; (6) safe to use with no risk of injury to tissues or transmission of disease; and (7) inexpensive (Pusateri, A. E., et al., J. Trauma, 60: 674-682 (2006)). With this list of ideal properties the question arises: Is there any deployed product capable of stopping or reducing groin arterial bleeding and preventing exsanguination that otherwise could not be controlled by the standard gauze dressing? The dressings evaluated by USAISR were the Army Field Dressing (a cotton product of long-standing use), Quikclot®, HemCon®, and Fibrin Sealant. Surface area coverage, sealant efficacy, adherence, and adsorption capacity are all important factors in this challenging area of hemostasis since the geometry and anatomical location of the wounds can vary greatly and factors into the success of patient survival. The Army Field Dressing, which is the standard field dressing used by the military, consists of two layers of gauze that wrap densely packed cotton. It absorbs a large volume of blood and the cotton strands stimulate platelet aggregation. The prohibitive price of Fibrin Sealant which consists of fibrinogen and thrombin ($500 to $1000 per dressing) prevents widespread deployment of this type of dressing. Quikclot® is a granular mineral zeolite that rapidly absorbs water in an exothermic reaction (Pusateri, A. E., et al., 2006). Some improvements on zeolite-impregnated dressings in the form of the kaolin-impregnated gauze (Quikclot® Combat Gauze) have been made. Bentonite (WoundStat™) also rapidly halts clotting (Ward, K. R., et al., J. Trauma, 63: 276-284 (2007); http://www.z-medica.com/zmedica/hemostasis_zmedica.asp).

Kaolin and bentonite are clay minerals which act as sealants; however, they do not produce an exothermic reaction. It is also noteworthy that recently the relative thrombogenic effects of these aluminum phyllosilicate clay minerals have been examined and questioned for their in vivo safety (Kheirabadi, B. S., et al., J. Trauma Injury, Infection and Critical Care, 668: 2 (2010)). However, it is important to understand their mode of action as blood flow sealants and in clotting. Furthermore, considerable concern was registered about systemic vascular thrombogenesis shown by bentonite granules since the material was tested as loose granules at the locus of the wound bed and resulted in occlusive thrombi. HemCon®, which is principally chitosan, has strong tissue adhesive properties that seal the wound and stops bleeding through promotion of platelet aggregation (Pusateri, A. E., et al., 2006). TraumaDex employs starch microspheres which seal blood flow upon application through a molecular sieve-like mechanism (Gegel, B. T., AANA Journal, 78(2): 115-120 (2010)).

Nonwoven dressings are typically composite materials containing more than one fiber, component, or layer (Das, D., et al., Text. Prog., 44: 1-84 (2012); Doh, S., et al., Fibers Polym., 14: 2176-2184 (2013)). In recent years nonwoven medical dressings have increased in usage both for absorbent hemostatic and chronic wound applications (Abou-Okeil, A., et al., 2012; Parikh, D. V., et al., Int. Nonwovens J., 8: 24-28 (1999)). A variety of natural and synthetic fibers have been reported and are used to promote hemostasis, including cotton, viscose, rayon/polyester, glass filament, chitosan, nylon, wool, and alginate (Barnett, S. E., and S. J. Varley, Ann. R. Coll. Surg. Engl., 69: 153-155 (1987); Fischer, T. H., et al., J. Biomed. Mater. Res. B, 91: 381-389 (2009); Groth, T., and W. Wagenknecht, Biomaterials, 22: 2719-2729 (2001); Gu, R., et al., Biomaterials, 31: 1270-1277 (2010); Hutchinson, R., et al., Cellulose, 20: 537-545

(2013); Islam, S., et al., J. Biobased Mater. Bioenergy, 7: 439-443 (2013); Jayakumar, R., et al., Biotechnol. Adv., 29: 322-337 (2011); Palm, M. D., and J. S. Altman, J. Dermatol. Surg., 34: 431-445 (2008); Segal, H. C., et al., J. Biomater. Appl., 12: 249-257 (1998); van der Weyden, E. A., Br. J. Community Nurs., 2005,10, doi:10.12968/bjcn.2005.10.Sup2.18175; Wang, H., et al., Blood Coagul. Fibrinolysis, 18: 555-558 (2007)). Topical hemostatic agents consisting of proteinaceous materials like wool (Islam, S., et al., 2013), and collagen and fibrin (Raccuia, J. S., et al., Am. J. Surg., 163: 234-238 (1992)) have also been reported to be very effective in promoting clotting. However, natural hemostatic fibers may be made from polysaccharide fibers (Rathinamoorthy, R., and I. Sasikala, Int. J. Pharm. Sci., 3: 38-44 (2013)), some notable ones include oxidized regenerated cellulose (Hutchinson, R., et al., 2013), carboxymethylcellulose (Doh, S., et al., 2013; Wang, H., et al., 2007), N-acetyl-glucosamine (Fischer, T. H., et al., J. Biomed. Mater. Res. A, 80: 167-174 (2007); Fischer, T. H., et al., Biomed. Mater., 2008, 3, doi:10.1088/1748-6041/3/1/015009), and starch (Bellamy, R. F., 1984), and these may be incorporated into materials that constitute structurally or process modified polysaccharides fibers. These polysaccharide fibers have also played an important role in understanding the relationship of structure to function in the design of hemostatic dressings, and they have been examined for their structure/function relationships in contact activation of blood coagulation (Fischer, T. H., et al., 2009; Fischer, T. H., et al., 2007; Fischer, T. H., et al., 2008). Bleached cotton has been utilized as a hemostatic for several centuries, and has been a stable of the standard First Aid kit. However, the usage of unbleached cotton as a hemostatic dressing has scarcely been explored.

Greige cotton refers to unfinished cotton fibers that have not been scoured and bleached. The potential to use greige cotton in nonwoven absorbent products has received increased attention based on innovations in cotton cleaning and nonwovens processes that open and expose the hydrophilic cellulosic component of greige cotton fiber to water absorption. FIG. 1 portrays a micrograph of hydroentangled greige cotton fibers that show how the outer layers of the fibers are loosened or lifted from the fiber during the hydroentanglement process. Previously it was shown that nonwoven greige cotton fibers, when compared with nonwoven bleached cotton, reduced the TEG (thromboelastography)-determined clotting time (FIG. 6) for both initial formation of fibrin and clot formation and increased the rate of clot formation while retaining approximately the same clot strength (Bellamy, R. F., 1984; Edwards, J. V., et al., A comparison of hemorrhage control and hydrogen peroxide generation in commercial and cotton-based wound dressing materials, IN Proceedings of 23rd Annual Meeting of the Wound Healing Society, SAWC Spring/WHS Joint Meeting, Silver (25th) Anniversary of the Wound Healing Society, Denver, Colo., 1-4 May 2013; Edwards, J. V., et al., J. Funct. Biomater., 5: 273-287 (2014)).

Moreover, recent work from USDA Agricultural Research Service in collaboration with H&H Medical has shown that nonwoven materials composed of greige cotton (True Cotton™ (TC)), and a combination of other fibers of varying polarity, accelerated blood clotting (Edwards, J. V., et al., A comparison of hemorrhage control and hydrogen peroxide generation in commercial and cotton-based wound dressing materials, IN Proceedings of 23rd Annual Meeting of the Wound Healing Society, SAWC Spring/WHS Joint Meeting, Silver (25th) Anniversary of the Wound Healing Society, Denver, Colo., 1-4 May 2013; Edwards, J. V., et al., 2014).

It is important to note that TrueCotton™ is a highly cleaned form of raw cotton. Originally we found that TC accelerated clotting over bleached and scoured cotton as judged by thromboelastography (TEG) (Edwards, J. V., et al., 2014).

We have now studied materials that have been blended with combinations of greige cotton, bleached cotton, cellulosics, and synthetic fibers for the development of hemostatic wound dressings that would likely be suitable for accelerating clotting in the treatment of vascular trauma.

SUMMARY OF THE INVENTION

Disclosed herein are single layered nonwoven wound dressings containing (1) about 5% by weight to about 95% by weight (e.g., 5% to 95%) non-scoured, non-bleached greige cotton fibers (preferably about 30% by weight to about 80% by weight (30-80), more preferably about 50% by weight to about 60% by weight (50-60)), (2) about 5% by weight to about 95% by weight (e.g., 5% to 95%) bleached cotton fibers (preferably about 20% by weight to about 70% by weight (20-70), more preferably about 20% by weight to about 30% by weight (20-30)), and (3) about 5% by weight to about 60% by weight (e.g., 5% to 60%) hydrophobic fibers (e.g., polypropylene, nylon) (preferably about 5% by weight to about 50% by weight (5-50), more preferably about 5% by weight to about 20% by weight (5-20)); all percentages adding up to 100 wt %. Also, multi-layered nonwoven wound dressings, containing (1) at least one inner layer containing (a) about 50% by weight to about 95% by weight (e.g., 50% to 95) non-scoured, non-bleached greige cotton fibers (preferably about 60% by weight to about 80% by weight (60-80); more preferably about 50% by weight to about 60% by weight (50-60)) and (b) about 5% by weight to about 50% by weight (e.g., 5% to 50%) hydrophobic fibers (preferably about 20% by weight to about 40% by weight (20-40), more preferably about 40% by weight to about 50% by weight (40-50)), all percentages adding up to 100 wt %, and (2) at least one outer layer containing (a) about 5% by weight to about 95% by weight (e.g., 5% to 95%) non-scoured, non-bleached greige cotton fibers (preferably about 30% by weight to about 80% by weight (30-80), more preferably about 50% by weight to about 60% by weight (50-60)), (b) about 5% by weight to about 95% by weight (e.g., 5% to 95%) bleached cotton fibers (preferably about 20% by weight to about 70% by weight (20-70), more preferably about 20% by weight to about 30% by weight (20-30)), and (c) about 5% by weight to about 60% by weight (e.g., 5% to 60%) hydrophobic fibers (e.g., polypropylene, nylon) (preferably about 5% by weight to about 50% by weight (5-50), more preferably about 5% by weight to about 20% by weight (5-20)); all percentages adding up to 100 wt %.

This summary is provided to introduce a selection of concepts in a simplified form that are further described below in the detailed description. This summary is not intended to identify key features or essential features of the claimed subject matter, nor is it intended as an aid in determining the scope of the claimed subject matter.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 5A shows placement of the inner layer of the dressing material on the outer layer of the dressing material followed by FIG. 5B which shows attachment of layers through needle punching and FIG. 5C shows two or three layered dressings released and cut to size.

DETAILED DESCRIPTION OF THE INVENTION

Figure 1:
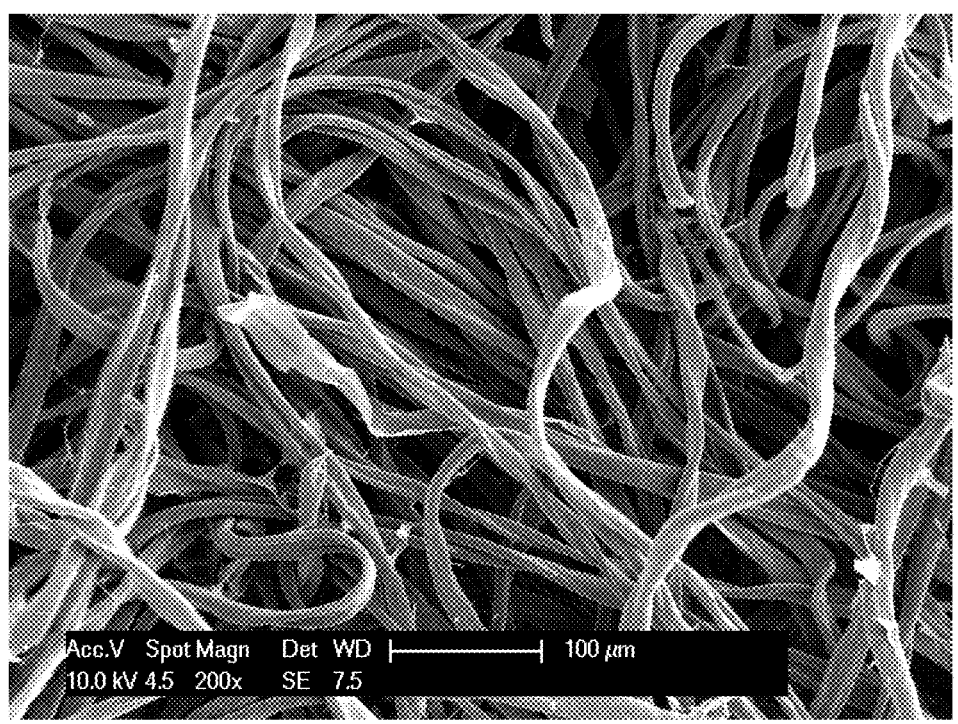
FIG. 1 shows a micrograph of hydroentangled cotton fibers that contain outer layers of the fibers that are removed during bleaching and scouring as described below.

Disclosed herein are single layered nonwoven wound dressings containing (1) about 5% by weight to about 95% by weight (e.g., 5% to 95%) non-scoured, non-bleached greige cotton fibers (preferably about 30% by weight to about 80% by weight (30-80), more preferably about 50% by weight to about 60% by weight (50-60)), (2) about 5% by weight to about 95% by weight (e.g., 5% to 95%) bleached cotton fibers (preferably about 20% by weight to about 70% by weight (20-70), more preferably about 20% by weight to about 30% by weight (20-30)), and (3) about 5% by weight to about 60% by weight (e.g., 5% to 60%) hydrophobic fibers (e.g., polypropylene, nylon) (preferably about 5% by weight to about 50% by weight (5-50), more preferably about 5% by weight to about 20% by weight (5-20)); all percentages adding up to 100 wt %. A preferred ratio of about 60/20/20 (e.g., 60/20/20) can be about 60 grams/20 grams/20 grams. The dressing may further contain minerals such as kaolin, zeolite, and pectin, wherein the pectin adheres the minerals to the fibers.

Also disclosed herein are multi-layered nonwoven wound dressings, containing (1) at least one inner layer containing (a) about 50% by weight to about 95% by weight (e.g., 50% to 95) non-scoured, non-bleached greige cotton fibers (preferably about 60% by weight to about 80% by weight (60-80); more preferably about 50% by weight to about 60% by weight (50-60)) and (b) about 5% by weight to about 50% by weight (e.g., 5% to 50%) hydrophobic fibers (preferably about 20% by weight to about 40% by weight (20-40), more preferably about 40% by weight to about 50% by weight (40-50)), all percentages adding up to 100 wt %, and (2) at least one outer layer containing (a) about 5% by weight to about 95% by weight (e.g., 5% to 95%) non-scoured, non-bleached greige cotton fibers (preferably about 30% by weight to about 80% by weight (30-80), more preferably about 50% by weight to about 60% by weight (50-60)), (b) about 5% by weight to about 95% by weight (e.g., 5% to 95%) bleached cotton fibers (preferably about 20% by weight to about 70% by weight (20-70), more preferably about 20% by weight to about 30% by weight (20-30)), and (c) about 5% by weight to about 60% by weight (e.g., 5% to 60%) hydrophobic fibers (e.g., polypropylene, nylon) (preferably about 5% by weight to about 50% by weight (5-50), more preferably about 5% by weight to about 20% by weight (5-20)); all percentages adding up to 100 wt %.

The single layered nonwoven wound dressings may be prepared by methods known in the art. For example, needle punched webs of the different fiber blends may be prepared. Then the needle-punched webs of the different fiber blends may be uniformly hydroentangled using, for example, a Fleissner MiniJet system where the system is equipped with one low water pressure jet head that wets the incoming feed web material on its top face, while two high water pressure jet heads alternatively impact the wetted substrate on either face. For all the fabrics, the low water pressure head may be set to inject the water at about 30 bars, and the two high water pressure heads may be set at about 60 to about 100 bars(e.g., 60 to 100). A 23 mesh screen or lower may be employed to modulate the fabric fenestration. The fabric production speed may be about 5 m per minute. The resulting hydroentangled fabric is dried (e.g., using a meter-wide, gas-fired drum dryer) and may be wound onto a tube (e.g., cardboard) to form a compact fabric roll.

A significant amount of the cotton fiber cuticle and primary cell wall components are retained during hydroentanglement, but it is expected that increasing pressure removes more of the non-cellulosic fiber components. The non-cellulosic components can potentially detach or be removed from the fiber matrix due to the force of the water jets that creates an entangled fiber network and also exerts pressure, shear and friction on the outer cuticle layer of the fiber to an extent that this hydrophobic component (contains waxes) of the fiber begins to loosen or even detach from the secondary cell wall of the fiber. We hypothesized that these cotton fiber components, which are partially retained from the hydroentanglement process, also play a role in the hemostatic activity of the dressing material since the hydrophobicity afforded by the waxes creates a negatively charged surface conducive to clotting acceleration.

As noted above, the dressing may further contain kaolin and pectin. Pectin is utilized to adhere the kaolin to the fabric. The addition of kaolin and pectin to the dressing may be achieved by any method known in the art, and one example is shown below.

Also disclosed are multi-layered (2-3 layers or more) nonwoven wound dressings which contain at least one inner layer containing about 50% by weight non-scoured, non-bleached greige cotton fibers and about 50% by weight hydrophobic (e.g., polypropylene, nylon) fibers and at least one outer layer containing about 30% by weight non-scoured, non-bleached greige cotton fibers, about 50% by weight bleached cotton fibers, and about 20% by weight hydrophobic (e.g., polypropylene, nylon) fibers (e.g., 30TC/50bl/20pp). Preparation of such multi-layers nonwoven wound dressings are described below and can be prepared by methods known in the art.

The materials of this invention may be nonwoven fabrics, which contain greige cotton along with other hydrophilic and hydrophobic fibers the combination of which can produce rapid clotting as defined by both thromboelastography (TEG) and in vitro clotting experiments. The materials when treated with a pectin/kaolin formulation also produce a more rapid clotting response sufficient to be considered a hemorrhage control dressing material.

Hydrophobic fibers include TrueCotton™ which is a non-scoured, non-bleached 100% natural greige cotton fiber which has been carefully mechanically cleaned to unprecedented levels. Since the cotton fiber has not been chemically altered, the natural waxes and oils remain on the fiber which allows for exceptional processing characteristics in any textile or nonwovens staple fiber manufacturing scheme. True Cotton™ fiber is naturally hydrophobic, which sets it apart from any cotton fiber previously used for consumer goods. True Cotton™ is 99.99% pure, meaning that 99.99% of foreign matter (e.g., cotton harvest contaminants in the form of cotton leaves, stems, and bracts; in other words, foreign matter includes anything in the way of trash that is carried over from the field to the ginning process) has been removed. The staple fiber length is about 19 to about 30 mm, hydrophobicity reflected in the water contact angle which is $140.9°+5.3$, and has a denier (micronaire) of about 3.5 to about 5.5 (e.g., 3.5 to 5.5; preferably about 4.0 to about 5.5 (e.g., 4.0 to 5.5)). Other hydrophobic fibers similar to TrueCotton™ may be used.

Other components (e.g., other hydrophilic or hydrophobic components) known in the art may be added to the wound dressing provided they do not substantially interfere with the intended activity and efficacy of the wound dressing; whether or not a compound interferes with activity and/or efficacy can be determined, for example, by the procedures utilized below. Hydrophilic fibers include, for example, bleached and scoured cotton, polyurethane, rayon, spandex, polyacrylate, flax, hemp, ramie, bamboo, alginate, chitosan, hyaluronan, regenerated cellulose, N-acetylglucosamine, and carbxoymethylcellulose. Hydrophobic fibers include, for example, polyolefin, polyester, polyacrylate, wool, glass filament, collagen, polypropylene and nylon.

As regards the term "wound dressing", as used in the context of the present invention, this in general in particular describes dressings for topical application onto external wounds, in order to prevent penetration of foreign bodies into the wound and to absorb blood and wound secretions. According to the invention, terms such as "wound plaster", "wound bandage" or "wound covering" can also be used synonymously. The wound dressings are not limited to a particular size or shape. The wound dressing composition may be multi-layered. For example, the wound dressing composition may be in the form of a trilayer composition, comprising two outer layers and an inner layer. The multi-layer wound dressing composition has been described herein as comprising first, second and third layers, although it may comprise further layers, such as fourth, fifth, sixth, seventh, eighth, ninth, tenth layers, or more. The further layers may comprise any of the features referred to herein in relation to the inner and outer layers.

The wound dressing may contain at least one active substance which is in particular selected from the group of bio statically or biocidally, and/or antimicrobially, acting active substances, disinfecting active substances, inflammation-inhibiting substances, analgesically active substances, styptic active substances (hemostyptics), and wound healing-promoting active substances. Thus in this connection it is preferred that the wound dressing is also treated with at least one biostatic or biocidal and/or antimicrobial and/or disinfecting and/or analgesic and/or inflammation-inhibiting and/or styptic and/or wound healing-promoting active substance. Equally it can be provided that the wound dressing contains at least one antimicrobial and/or disinfecting and/or analgesic and/or inflammation-inhibiting and/or styptic and/or wound healing-promoting active substance. In this connection, it has been found particularly advantageous if the active substance has a biocidal or biostatic action, in particular a bactericidal or bacteriostatic and/or a fungicidal or fungistatic and/or virucidal or virostatic action.

"Optional" or "optionally" means that the subsequently described event or circumstance may or may not occur, and that the description includes instances in which said event or circumstance occurs and instances where it does not. For example, the phrase "optionally comprising an antimicrobial agent" means that the wound dressing may or may not contain an antimicrobial agent and that this description includes wound dressings that contain and do not contain an antimicrobial agent. Also, by example, the phrase "optionally adding an antimicrobial agent" means that the method may or may not involve adding an antimicrobial agent and that this description includes methods that involve and do not involve adding an antimicrobial agent.

Other compounds (e.g., antimicrobial agent) may be added to the wound dressing provided they do not substantially interfere with the intended activity and efficacy of the wound dressing; whether or not a compound interferes with activity and/or efficacy can be determined, for example, by the procedures utilized below.

By the term "effective amount" of a compound or property as provided herein is meant such amount as is capable of performing the function of the compound or property for which an effective amount is expressed. As will be pointed out below, the exact amount required will vary from process to process, depending on recognized variables such as the compounds employed and the processing conditions observed. Thus, it is not possible to specify an exact "effective amount." However, an appropriate effective amount may be determined by one of ordinary skill in the art using only routine experimentation.

While this invention may be embodied in many different forms, there are described in detail herein specific preferred embodiments of the invention. The present disclosure is an exemplification of the principles of the invention and is not intended to limit the invention to the particular embodiments illustrated. All patents, patent applications, scientific papers, and any other referenced materials mentioned herein are incorporated by reference in their entirety. Furthermore, the invention encompasses any possible combination of some or all of the various embodiments and characteristics described herein and/or incorporated herein. In addition the invention encompasses any possible combination that also specifically excludes any one or some of the various embodiments and characteristics described herein and/or incorporated herein.

The amounts, percentages and ranges disclosed herein are not meant to be limiting, and increments between the recited amounts, percentages and ranges are specifically envisioned as part of the invention. All ranges and parameters disclosed herein are understood to encompass any and all subranges subsumed therein, and every number between the endpoints. For example, a stated range of "1 to 10" should be considered to include any and all subranges between (and inclusive of) the minimum value of 1 and the maximum value of 10 including all integer values and decimal values; that is, all subranges beginning with a minimum value of 1 or more, (e.g., 1 to 6.1), and ending with a maximum value of 10 or less, (e.g. 2.3 to 9.4, 3 to 8, 4 to 7), and finally to each number 1, 2, 3, 4, 5, 6, 7, 8, 9, and 10 contained within the range.

Unless otherwise indicated, all numbers expressing quantities of ingredients, properties such as molecular weight, reaction conditions (e.g., reaction time, temperature), percentages and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. As used herein, the term "about" refers to a quantity, level, value, or amount that varies by as much as 10% to a reference quantity, level, value, or amount.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described.

The following examples are intended only to further illustrate the invention and are not intended to limit the scope of the invention as defined by the claims.

EXAMPLES

Thromboelastography: Citrated bovine blood was used for TEG analysis. Blood analysis: 240 µl bovine blood and 20 µl $CaCl_2$ were added to the sample cup and the run was begun. Alternatively, 20 µl citrated saline was added to the sample cup. 990 µl blood was gently mixed with 90 µl $CaCl_2$. 240 µl of this was immediately added to the cup and the run was begun. Fabric samples: 1 mg fabric was added to the sample cup with 20 µl citrated saline. 990 µl blood was gently mixed with 90 µl $CaCl_2$. 240 ul of the blood mix was added to the sample cup and the run was begun.

Wicking Experiments: Wicking data were created by hanging the fabric sample in either water or electrolyte (the same electrolyte used in the absorbance testing) and recording the mass reduction of the liquid vs. time. Experiments were carried out for 5 minutes. Data points were taken more frequently in early times to record initial liquid uptake. Since the liquid uptake will depend on the amount of contact between liquid and fabric, mass losses were divided by the width of the fabric sample to normalize that variable out of the calculation. Uptake units of g (liquid)/cm (fabric) were thus derived. Liquid uptake vs. time data were plotted in OriginPro® 2016. OriginPro® has built-in curve fitting routines, and although run times were 5 min, uptake data were not well-fit by any of the built-in routines or the user defined routine that was created for these measurements. For many of the tests the fits were evaluated from data taken up to 2 and at 3 minutes. In general data generated in the first 2 minutes of a wicking test gave better fits (higher $R^2$) and all data reported as "regression" were 2 minute fits. The Uptake data shown in FIG. 10 were calculated from a regression line using data from 0-120 seconds. Component fabric densities were calculated from the fabric density multiplied by the fraction of that component in the blend. For multilayer fabrics a straight average was used.

Absorbency: A sample, consisting of 4 coupons, was measured and weighed so that a "density" in $g/cm^2$ was determined. The coupons were soaked in a 142 mM NaCl/2.5 mM $CaCl_2$ solution, weighed, centrifuged, and reweighed. The mass changes at the various steps in the procedure allowed for the determination of the quantities of water that can be taken up and held. Although absorbency typically has been reported as g $H_2O$/g fabric, with the density value the absorbency in $g/100\ cm^2$ can also be calculated.

Electrokinetic analysis: The determination of the ζ-potential was carried out with the Electro Kinetic Analyzer (Anton Paar, Ashland, Va.) using the Cylindrical Cell developed for the measurement of fibrous samples. When a fiber absorbs liquid and swells, the surface charges become farther separated and the absolute value of its ζ-potential decreases. Two kinds of measurements were made on each sample: (1) swell tests to measure the rate and extent of fiber swelling (at a given pH) and (2) a pH titration in which the swelling is measured as a function of pH. All ζ-potential measurements were made in a 1 mM KCl electrolyte.

In the electrokinetic apparatus the streaming potential was measured and the zeta potential determined from the Smoluchowski equation:

$$\varsigma = \frac{dU}{dp} \frac{\eta\kappa}{\varepsilon_r\varepsilon_0} \qquad (1)$$

Where U is the streaming potential, the potential generated when an electrolyte is forced to flow over a stationary charged surface, p the pressure, $\varepsilon_r$ and $\varepsilon_o$ the dielectric constant and the vacuum permittivity, η the viscosity, and κ is the conductivity of the measuring fluid. Surface conductivity of the fibrous samples was not taken into account.

pH titrations were performed over a pH range of 1.8 to 11 to ensure recording both the isoelectric point (IEP) and the plateau potential. The IEP is the pH at which $\zeta=0$ and provides insights into the surface association/dissociation processes.

Swell tests and pH titrations were carried out on hydroentangled nonwoven fabrics, cotton-polyester blends, cotton-nylon blends, or cotton and cotton by-products. Swell tests were performed during which the zeta potential, $\zeta$, was measured against time. These data were subsequently fit to a first-order decay equation $$-\frac{d\zeta}{dt} = k(\zeta - \zeta_\infty)$$

where $\zeta_\infty$ equals $\zeta$ at infinite time and k is the decay constant. Integrating $$\ln\left(\frac{\zeta - \zeta_\infty}{\zeta_0 - \zeta_\infty}\right) = -kt$$

$\zeta_0$ is the integration constant and is $\zeta$ at time=0, i.e., the time when the fiber first contacts the electrolyte. A regression routine was developed to evaluate swell data for $\zeta_0$, $\zeta_\infty$ and k. $\zeta_0$ and $\zeta_\infty$ were then used to calculate a $\Delta\zeta$.

$$\Delta\zeta = \frac{\zeta_0 - \zeta_\infty}{\zeta_0} \quad (2)$$

A mathematical regression routine was written for MathCad and was used to determine three parameters in swell tests: $\zeta_0$, $\zeta_\infty$, and k.

Figure 3:
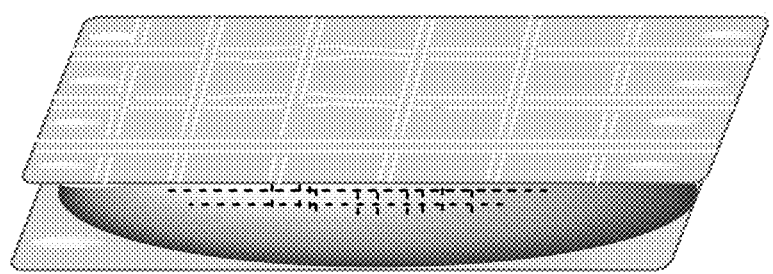
FIG. 3 shows one embodiment of the invention as described below where the outside layers (gray top and bottom layers) may contain a high percentage of blended hydrophilic fibers (e.g., 80% bleached cotton/20% TC) or it may contain a combination of nonpolar and polar fibers (e.g., 33% bleached cotton/33% TC/33% polypropylene (PP)), whereas the inner layer (depicted as the purple shade) contains a more hydrophobic component (e.g., 50% TC/50% PP) which promotes both enhanced uptake of blood and accelerates clotting.

Preparation of Single Layered Nonwoven Material. Hydroentanglement of fibrous webs into nonwoven fabric structures: A commercially available bale of pre-cleaned greige cotton was acquired from T. J. Beall, LLC (Greenwood, Miss.). Polypropylene fibers were acquired commercially. A bleached version of True Cotton™ was also acquired from T. J. Beall. The needle punched webs of the different fiber blends were uniformly hydroentangled using a Fleissner MiniJet system (FIG. 3). The system was equipped with one low water pressure jet head that wets the incoming feed web material on its top face while two high water pressure jet heads alternatively impact the wetted substrate on either face. For all the fabrics, the low water pressure head was set to wet the fabric at 30 bars of water pressure and the two high water pressure heads were set at either 60, 80, or 100 bars. The fabric production speed was 5 meters per minute. The resulting hydro-entangled fabric was dried using a meter-wide, gas-fired, through-Drum Dryer and wound onto a cardboard tube to form a compact fabric roll. The hydroentangling line utilizes municipal water that is passed through a reverse osmosis filter that is set to give a water hardness of 70 to 110 PPM.

Figure 4:
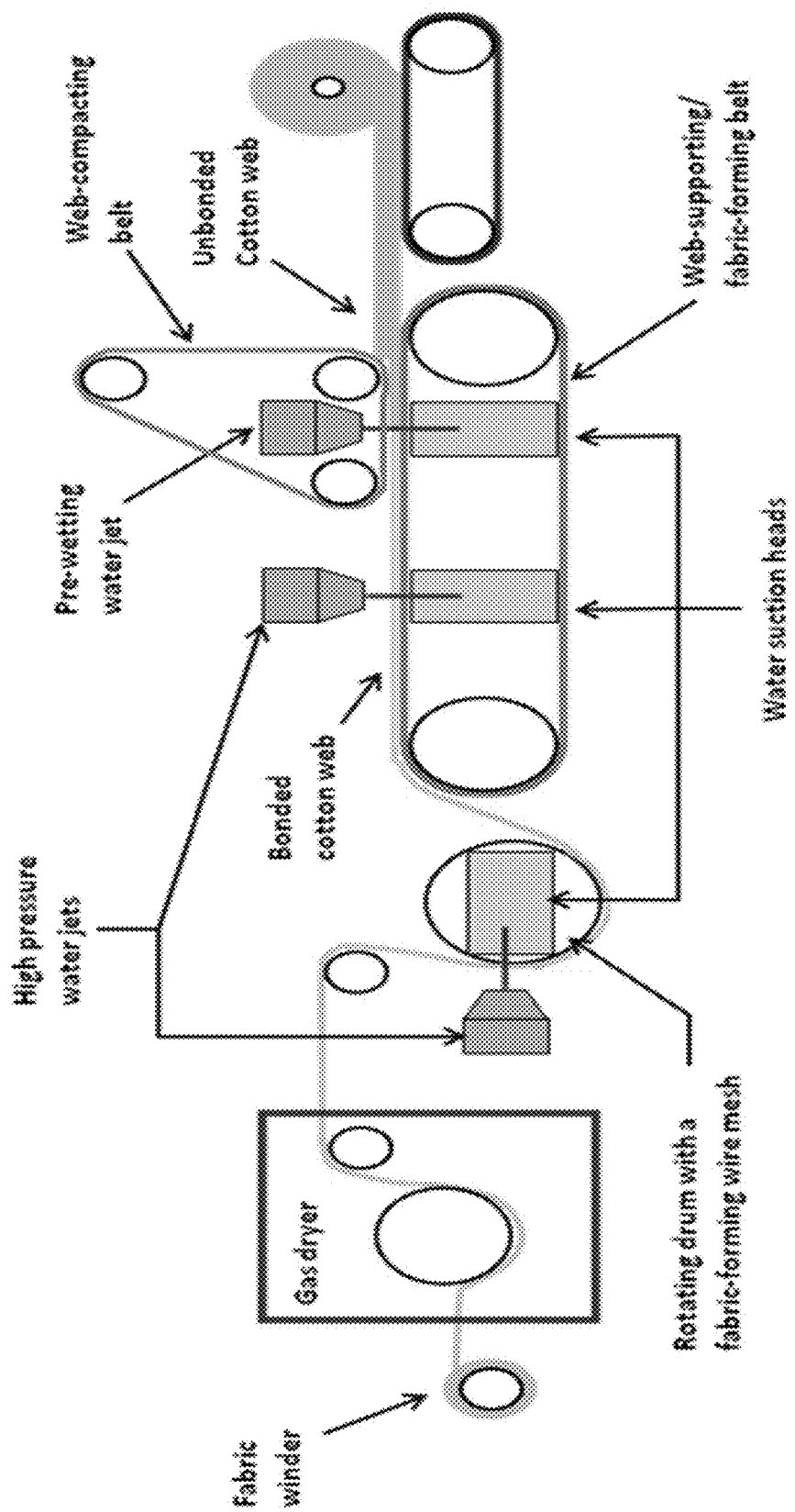
FIG. 4 shows a diagram of a nonwovens hydroentanglement line and an outline schematic of the Fleissner MiniJet system used in our study as described below.
Figure 5A:
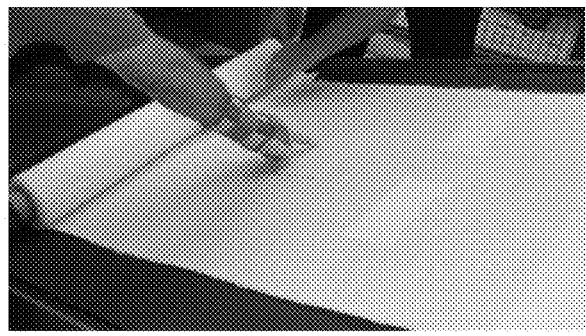
FIG. 5A, FIG. 5B, and FIG. 5C by way of images demonstrates how the multilayered dressings were prepared on a needle punch line as described below, and demonstrates.
Figure 5B:
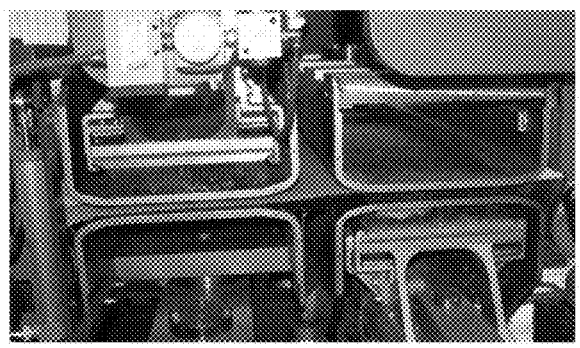
Figure 5C:
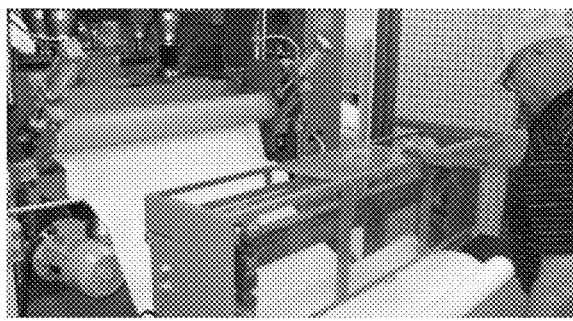

Multilayered Dressing: Dressings were assembled by a combination of hydroentanglement and needle punch. FIG. 4 illustrates that approach to preparation of the multilayered dressings. As shown in FIG. 5A-C, a square coupon of fabric assigned as the inner layer of the dressing was placed on a needle punched fabric containing the outer layer and a sheet of the outer layer composition was placed over it. The resulting composite was placed through a needle punch operation to fuse the fabric layers.

Preparation of Kaolin Treated Fabrics. Materials: The reagents pectin from citrus peel, galacturonic acid >74.0% (cat #P9135), kaolin, and hydrated aluminum silicate (cat #K7375) were ordered from Sigma-Aldrich (St. Louis, Mo.). The types of hydroentangled fabric treated were B2 (30% True Cotton© greige cotton/20% polypropylene/50% bleached TC), B6 (100% bleached TC) and B5S-3 (33% PA6 (nylon 6.6)/33% TC/33% bleached TC). Millipore ultra-pure water was used to make solutions. C.S. Osborne No. 149 Arch Punch (various sizes) were used to cut testing samples of the treated fabric swatches.

Method: Swatches, 4×6 inches, were cut of each fabric. Stock solution, 150 mL, of pectin, 1% (w/v) or 10 mg/mL, was made by heating at 40-50° C. while stirring. The solution sat overnight in the refrigerator. Next, the series of ratio solutions were made adding the appropriate amount of kaolin powder to 25 mL of 1% pectin; 1:0.5 refers to 10 mg of pectin to 5 mg of kaolin per mL of water. Subsequent ratios were made: 1:1, 1:2.5, 1:5 and 1:10. The pectin-kaolin solution was stirred at room temperature until a milky suspension formed. Each solution was vortexed before treatment of fabric to mitigate settlement. In a container, 5 mL of the appropriate solution was used to wet and saturate each fabric piece, including a pectin only solution for each fabric. Excess liquid was gently squeezed out or blotted. The saturated fabric pieces were placed flat on a metal surface with venting holes and placed into a force draft oven set at 85° C. and dried for 5 minutes. The samples were then allowed to equilibrate/condition overnight and then weighed. We found that placing the fabric in a plastic sleeve facilitated cutting out samples for testing. After drying in the oven, the samples were somewhat stiff. The 1:10 ratio left residue (kaolin) on the metal drying surface and some parts of treatment separated from the fabric (residue) during its removal. These samples (P:K, 1:0.5) were air dried at room temperature on a coated wire rack (non-absorbing) at least overnight. P:K=1:1 to 1:2.5 is preferred.

Another approach to applying clay minerals as kaolin in combination with zeolite employed the following formulations in (1:3:1, pectin:kaolin:zeolite) as shown in the Table below:

| Sample ID | Sample Description* | Before wt. (g) | Padded wt.(g) | After wt. (g) | % Wet Pickup | % Add-On |
|---|---|---|---|---|---|---|
| 072418-1 | Pectin only | 0.5240 | 2.95 | 0.5438 | 463.0 | 3.8 |
| 072418-2 | pectin: zeolite UF | 0.5254 | 3.03 | 0.5742 | 476.7 | 9.3 |
| 072418-3 | pectin: zeolite 40 mesh | 0.6116 | 3.66 | 0.6781 | 498.4 | 10.9 |
| 072418-4 | pectin: lion kaolin | 0.5744 | 4.17 | 0.7049 | 626.0 | 22.7 |
| 072418-5 | pectin: lion kaolin: zeolite UF | 0.5659 | 3.32 | 0.6833 | 486.7 | 20.7 |
| 072418-6 | pectin: lion kaolin: zeolite 40m | 0.5437 | 3.22 | 0.6851 | 492.2 | 26.0 |
| 072418-7 | pectin: electros kaolin | 0.5933 | 3.22 | 0.6869 | 442.7 | 15.8 |

-continued

| Sample ID | Sample Description* | Before wt. (g) | Padded wt.(g) | After wt. (g) | % Wet Pickup | % Add-On |
|---|---|---|---|---|---|---|
| 072418-8 | pectin: electros kaolin:zeoliteUF | 0.6042 | 3.94 | 0.7717 | 552.1 | 27.7 |
| 072418-9 | pectin: electros kaolin:zeolite40m | 0.5473 | 4.48 | 0.7338 | 718.6 | 34.1 |

*PEC = pectin; LK = lion Kaolin; EK = electros kaolin; Z = zeolite; UF = ultra fine; 40m = 40 mesh The samples gave the TEG-determined clotting results shown in the table below:

| Sample | R min | SD | k min | SD | Angle deg | SD | MA mm | SD |
|---|---|---|---|---|---|---|---|---|
| bovine blood | 14.8 | 0.6 | 4.0 | 3.6 | 34.2 | 8.4 | 71.8 | 0.6 |
| 60/20/20, GC/BL/PP | 11.6 | 2.1 | 5.2 | 1.1 | 41.6 | 5.5 | 72.2 | 0.7 |
| Hem - Pectin 10 mg/ml | 9.8 | 0.5 | 6.2 | 1.2 | 33.6 | 8.6 | 72.5 | 1.3 |
| Hem - Pec:LK 10:30 mg/ml | 3.7 | 0.0 | 0.8 | 0.0 | 69.4 | 10.7 | 69.9 | 2.0 |
| Hem - Pec:EK 10:30 mg/ml | 4.0 | 0.3 | 0.9 | 0.1 | 67.8 | 11.2 | 69.5 | 0.0 |
| Hem - Pec:ZuF 10:10 mg/ml | 5.4 | 0.8 | 1.5 | 0.5 | 64.4 | 5.9 | 68.0 | 4.1 |
| Hem - Pec:LK:ZuF 10:30:10 | 4.6 | 0.4 | 0.9 | 0.0 | 74.2 | 0.0 | 69.6 | 0.8 |
| Hem - Pec:EK:ZuF 10:30:10 | 3.8 | 0.1 | 0.8 | 0.0 | 78.4 | 2.9 | 69.4 | 2.1 |

Abbreviations
pec = pectin
LK = Lion Kaolin
EK = electros kaolin
Zuf = green zeolite (ultra fine)

One of our dressing design objectives was to prepare materials made of cotton-based fibers that are combined with other synthetic and/or natural fibers prepared in a manner that gives a nonwoven wound dressing product which accelerates clotting while having superior wicking and absorption capacity properties.

The hemostatic functionality of the dressing is multifactorial and results from fiber components to gross material structure and has fiber composition with properties of polarity, wettability, and swelling, as well as material structure (mesh, fenestration, density) that work synergistically to enhance clotting. The fiber composition is also determined by the hydroentanglement process which operates under varying pressures that remove or loosen waxes and pectin from the outer cotton fiber layers (FIG. 1). In this study, materials have principally been prepared in the initial screening at varying hydroentanglement pressures (e.g., 60, 80, and 100 mbar). Subsequent layered dressings also incorporated a needle punched layer to improve on loft (the properties of bulk and resilience in a fabric) and wicking properties. A significant amount of the cotton fiber cuticle and primary cell wall components are retained during hydroentanglement, but it is expected that increasing pressure removes more of the non-cellulosic fiber components. The non-cellulosic components can potentially detach or be removed from the fiber matrix due to the force of the water jets that creates an entangled fiber network and also exerts pressure, shear and friction on the outer cuticle layer of the fiber to an extent that this hydrophobic component (contains waxes) of the fiber begins to loosen or even detach from the secondary cell wall of the fiber. We hypothesized that these cotton fiber components, which are partially retained from the hydroentanglement process, also play a role in the hemostatic activity of the dressing material since the hydrophobicity afforded by the waxes creates a negatively charged surface conducive to clotting acceleration. One goal of our cotton-based hemostatic dressings was to combine fiber blends that would give accelerated clot formation by virtue of the polarity and charge of fiber composition and design synergistic with overall dressing material construction and based on promotion of high absorption capacity and wicking properties to yield advanced hemostatic dressings for use on a traumatic wound.

Single Layered Dressing: The approach to developing the single layered dressing was divided into three phases: (1) The initial phase involved screening nonwoven samples that varied in composition, density, and mesh, and which were contracted from a commercial nonwovens mill. The preliminary study on industrially produced fabrics, where these fabrics were identified, involved examining variations of material composition with Tencel/greige cotton and greige cotton/polypropylene, and the principle variation in composition produced in the USDA Southern Regional Research Center nonwovens mill, and involved blending different ratios of greige cotton, bleached cotton, and polypropylene, and a small study where nylon fibers were blended with greige cotton. These samples were tested for their activity against standards, including Combat Gauze®, Kerlix™ gauze, and rayon polyester gauze with the TEG results shown in Table 1. These were blends of True Cotton™ and Tencel® (made from the natural cellulose found in wood pulp). Due to the tightly controlled iterative changes in density, mesh, and composition of this series of fabrics, these blends were deemed of interest to assess the effect of overall fabric structure on fiber-promoted clotting. From this group of samples a lead was determined based on thromboelastography results. Thus, the best hemostatic performing fabrics from the industrially produced series were UTF-1H (85% greige cotton/15% Tencel) and greige cotton:polypropylene (50:50). The composition of this material and accompanying fabric weight and aperture were utilized in the design components. As shown in Table 1, UT-F-1H was found to exhibit the best fiber initiated clotting values.

Surprisingly, from the initial series of experiments based on TEG results, it appeared that clotting function was affected by composition, mesh and density, i.e., the fiber samples' composition, higher fenestration, and lower density fabrics appeared to perform better in the Fleissner samples utilized (Table 1).

Thus, we determined that the hydroentanglement process should be performed with a 23 mesh screen or lower (down to 17 mesh screen) to investigate clotting properties of fabrics with relatively low fenestration. A 23 mesh screen was added to the hydroentanglement line and a series of fabric blends containing greige cotton were prepared.

Series of Single Layered Materials Produced at USDA: The ensuing series of fabric variations contained greige cotton (TC), bleached TC, and polypropylene. The TEG clotting results of the most promising of these fabrics are shown in Table 2. The TEG clotting results of fabric designs subsequent to these are shown in Table 3 and Table 8.

As shown in Table 4, composition ratios of greige cotton: bleached cotton: polypropylene were varied from hydrophilic polarity to increasing hydrophobicity as identified and confirmed in the electrokinetic analysis, i.e., from 100% bleached to 100% greige or 50% greige: 50% polypropylene. The correlation observed for the fiber composition was found to be consistent with increased clotting velocity paralleling increasing negative Zeta Plateau values. Thus more of both greige cotton and more hydrophobic fibers like polypropylene surprisingly gave an increase in negative zeta potential compared with 100 percent bleached cotton. Examples of this are seen with 50:50 Greige cotton: Polypropylene, Zeta Potential=−48 mv, and 30/50/20, greige cotton/bleached cotton/polypropylene, Zeta Potential=−37 mv.

Attempts to correlate electrokinetic data with clotting mostly revealed surprisingly more favorable correlations between swell ratio or $\Delta\zeta$ and differential clotting values between blood controls and fabrics. It is noteworthy that the increased swelling of the fibers which typically parallels increased Zeta Potential was also surprisingly associated with short clotting times. We surprisingly identified a more negative $\zeta_{plateau}$ tended to correlate with more rapid clotting as reflected in TEG data and as shown when the TEG results (Table 3) of fibers of differing polarities were correlated with the electrokinetic data (Table 4). Correlations have been made between increased swell ratio, hydrophobicity, and accelerated clot formation (k value) with a tightly controlled set of samples.

Nylon-Containing Materials: By adding nylon 66 fibers as a hydrophobic component, a similar trend was observed to that of the polypropylene-containing greige cotton/bleached cotton composites. The results of the TEG clotting profiles for these types of fibers and the related electrokinetic results are shown in Table 5. It is also surprisingly notable that nylon-containing fabrics showed some relation between increased swell ratio and clotting, and increasing True Cotton™ and polypropylene surprisingly tended to increase swell ratio as well as shown in Table 5.

Figure 6:
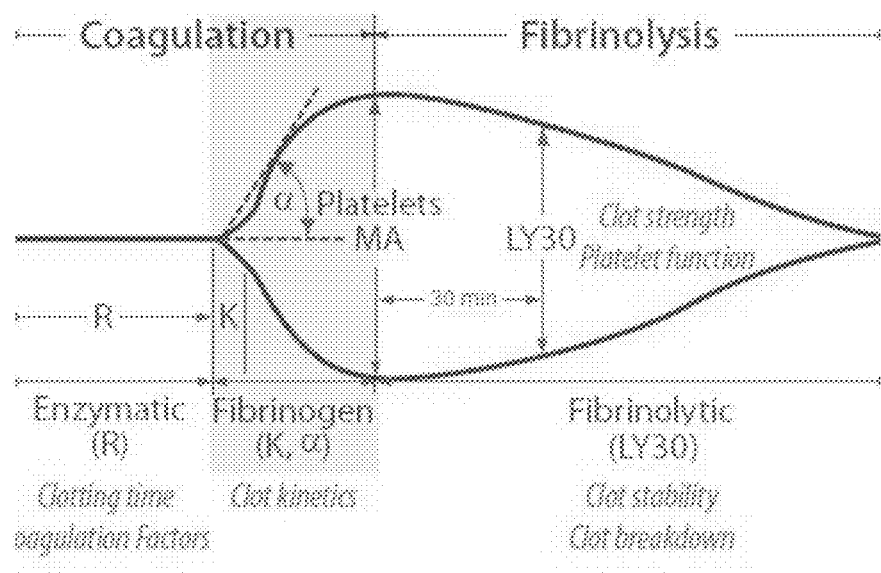
FIG. 6 shows a diagram of a thromboelastography profile as described below: R is time to fibrin formation, K is time from fibrin formation to clot formation, angle is rate of clot formation, and MA is strength of clot.
Figure 9:
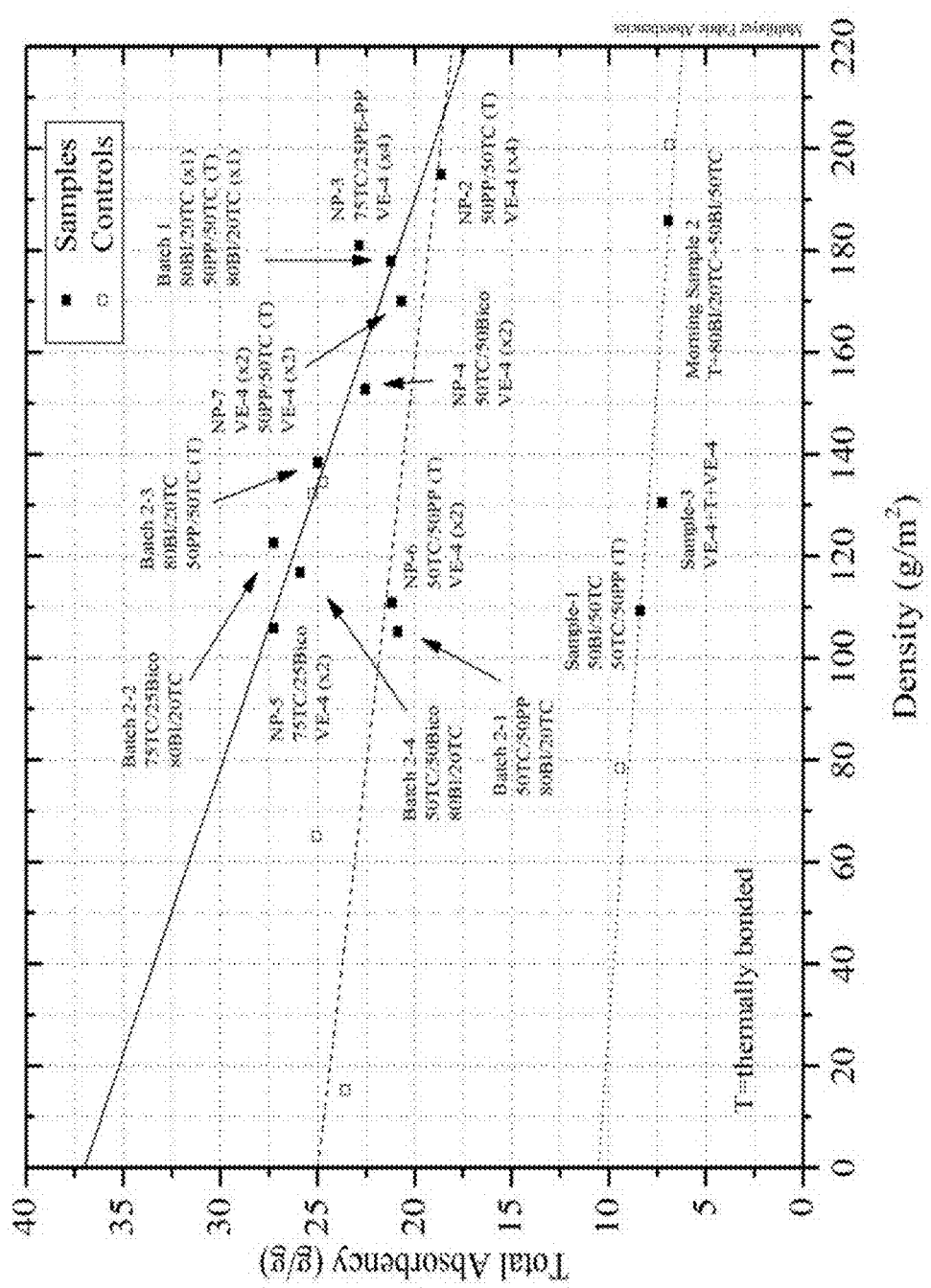
FIG. 9 shows a plot of total absorbency of physiological saline solution versus fabric density as described below (y-axis is grams of saline solution absorbed per gram of fabric (g/g), versus x-axis which is grams of fabric/meter squared (g/m$^2$)). VE-4=30TC/50bl/20pp (TC=True Cotton, bl=bleached cotton, pp=polypropylene). See Table 9 for a description of fabric composition.
Figure 10:
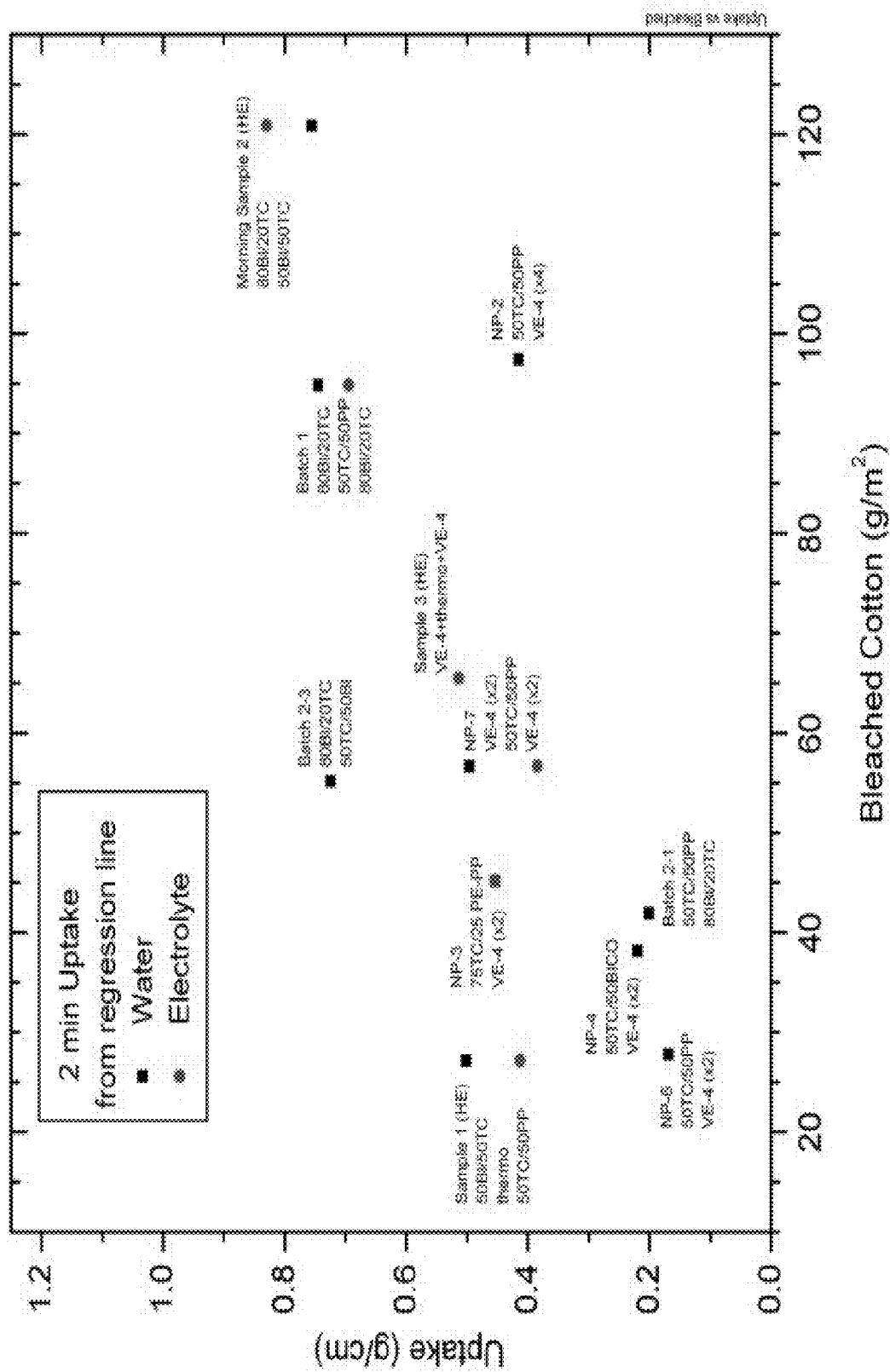
FIG. 10 shows a plot of density (gram/square meter) of bleached cotton versus fabric uptake in grams/cm over a two minute period as described below. Red indicates physiological saline and black deionized water.

Absorbency Considerations and Lee White Clotting Assay: Absorption capacity and wicking plays a key role in clotting efficiency when textile materials are employed as hemostatic dressings. Thus, these parameters were matched with the fiber TEG data (Table 1 & Table 3) and examined in the context of electrokinetic data (Table 4) to determine lead materials for hemostatic dressing activity and further testing in whole material clotting tests. The results are given both in terms of fabric weight and area. Determinations were made with over sixty fabric samples on the whole fabric, and on the amount of physiological saline retained between the fibers (inter-fiber) and within the fibers (intra-fiber). Surprisingly, as seen in Table 6, the absorption capacity varied from two grams per gram fabric to over seventeen grams per gram fabric. Higher absorption capacity should influence increased clotting and enable stabilization of clot formation. Thus the fabrics having the highest absorption capacity (for example, 30TC/50bl/20pp) should also influence clot formation (see above list of lead samples from TEG study). It was surprising that the 30TC/50/Bl/20PP fabric had a high absorption capacity given the hydrophobicity reflected in both the negative zeta potential as well hydrophobic composition. However, its absorption capacity was, without being bound by theory, most likely due to retention of rapidly wicked saline. Surprisingly this phenomenon appeared to influence the ability of the material to accelerate clotting as shown in the Lee White clotting results in Table 7 where the same material was found to initiate clotting more efficiently than any other material examined in the Lee White clotting assay using fresh porcine whole blood. Surprisingly, this may also be due to its influence on platelets which are more intact in fresh whole blood (i.e., less so in bovine blood reported in the TEG assay). Fabrics with high absorption capacity and wicking response were selected as the outer layer of the layered dressing motifs. A plot of the absorption capacities versus fabric density of the layered dressings is shown in FIG. 9 and a plot of physiological saline uptake vs. ratio of bleached cotton is shown in FIG. 10. As shown in FIG. 9, the three layered fabric containing an outer layer of 30TC/50bl/20pp has approximately the same absorption capacity and density as the one with 80bl/20TC. Both motifs have a 50TC/50PP as the inner layer. Hence it is not obvious that the 50TC/50PP fabric would be a suitable clotting agent since, due to its hydrophobicity, it tends to repel water or has a high contact angle creating more buoyancy than absorption of whole blood. Surprisingly, however, when placed as the inner layer of a multilayer dressing and having an outer layer that has high absorption capacity the compositions work synergistically to rapidly induce and stabilize clotting. However, surprisingly, as shown in FIG. 6, the rate of uptake of physiological saline by the 80bl/20TC-containing dressing was approximately 250 mg/cm more than the 30TC/50bl/20pp-containing dressing over a 2 minute period, and illustrated the importance of the more hydrophilic component of bleached cotton to facilitate solution uptake. Given this observation it was surprising that the 30TC/50Bl/20PP (B2) fabric was found to accelerate blood clotting, as shown in fresh blood assessed in the Lee White clotting assay demonstrated in Table 7, more rapidly than more hydrophilic fabrics (i.e., 100% bleached cotton).

Figure 11:
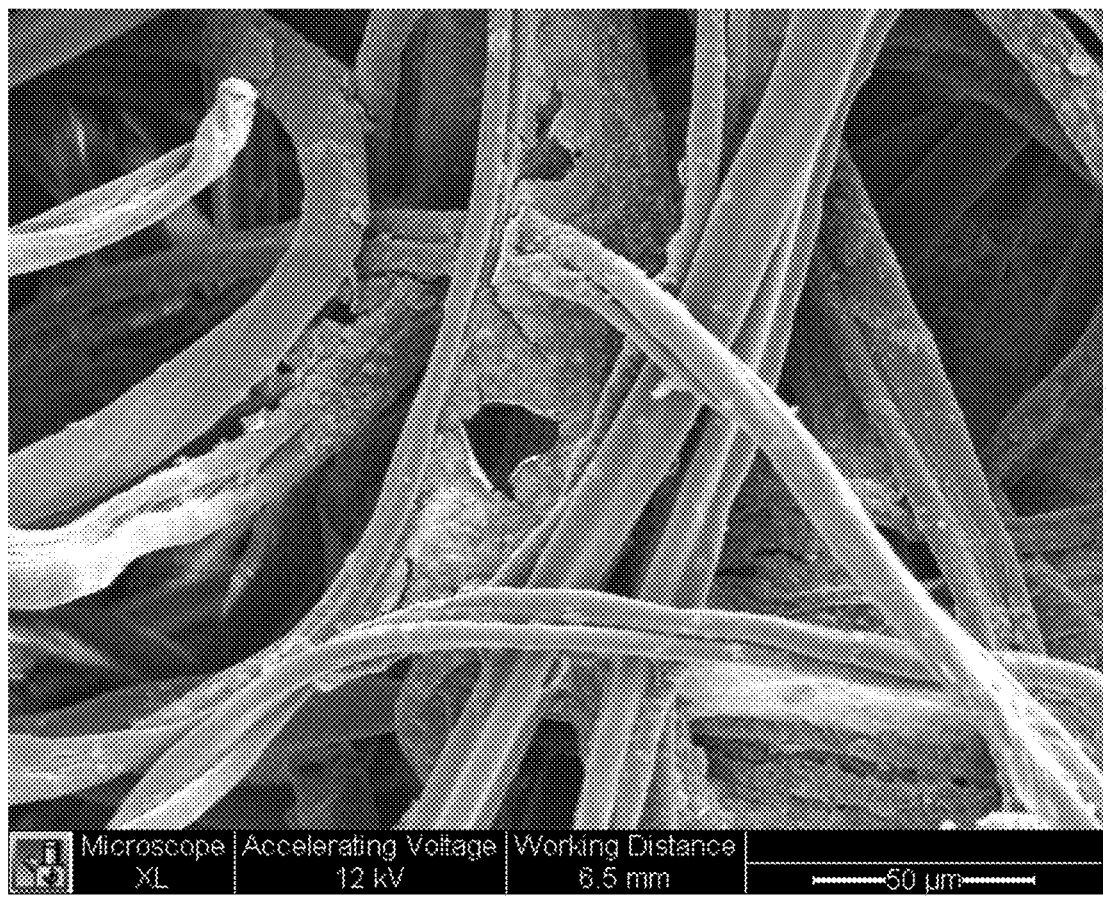
FIG. 11 shows scanning electron microscopy (SEM) of Pectin/Kaolin-Treated Fabric as described below.

Kaolin-Treated Materials and Their TEG and Lee White Clotting Assay Results: Table 8 shows the results of two kaolin-treated materials at varying material:pectin/kaolin (P:K) ratios. Pectin was utilized to adhere the kaolin to the fabric. The pectin/kaolin formulation adhered to the fabric by forming a coating both between and upon the fibers of the fabric as shown in the SEM in FIG. 11. Based on these results the P:K formulation was effective at doses as low as 1:1. On the other hand, as shown in Table 7, the Lee White clotting assay revealed that the 1:2.5 ratio or greater (1:10) formulation was surprisingly required for optimal clotting efficiency. Thus, the results of the Lee White clotting experiments demonstrated that pectin/kaolin formulations applied to sample B2 (30TC/50BL/20PP) materials work well from 1:2.5 by weight of material to formulation or greater. However it also works well for other combinations of fibers that include hydrophilic and hydrophobic fibers, i.e. bleached cotton, polypropylene, nylon as shown in the clotting results in Table 8a. It was noted that other clay minerals or transition metal salts may be used with a similar efficacy as shown in the TEG results in Table 8b.

Summary Highlighting Single Layered Lead Fabrics Based on TEG Data: TEG results for fiber evaluations were subject to considerable variation due to differences in bovine blood clotting. However, where fiber compositions produced significant effects on R, K, and α that appeared promising, repeat experiments with new batches of bovine blood were examined for confirmation. Materials that showed the most promise based on differential clotting values of R and K in the results depicted in Tables 1-5 were as follows:

B10 S-2 (33TC/33bl/33pp) 100b-37.9*,
B10 (50TC/50pp) 60b-65*,
100% TC-60b-35*,
B6 (0TC/100bl/0pp) 60b-27.6*,

UTF 1H*=85TC/15 Tencel,
B1 S-2 (75PA6.6/25TC) 60b-38.2*,
B2 S-2 (15PA6.6/85TC) 60b-38.8*,
B2 (30TC/50bl/20pp) 100b-34.0*,
B7 (100TC/0bl/0pp) 80b-36.6*,
B6S3-50% PA6.6, 50% TC-60 bar-HW, and
B2S3-75% PA6.6, 25% TC-80 bar-LW.

Figure 7:
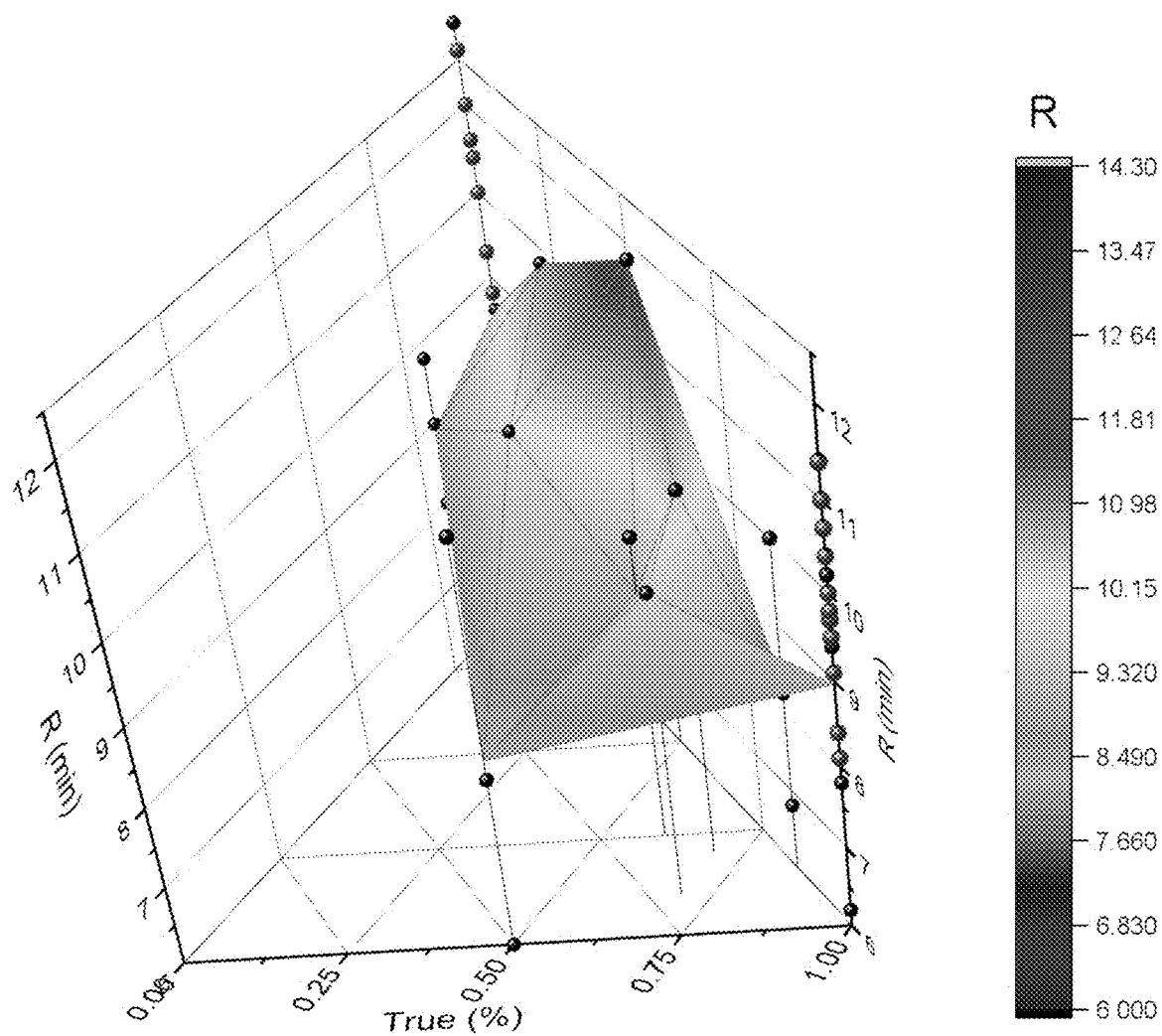
FIG. 7 shows 3-D graphical methods as described below that were employed to identify trends in clotting in terms of the three component composition. Thus, variation in blood clotting properties due to compositions (i.e., of TC, bleached cotton, and polypropylene) in hydroentangled non-woven fabrics are visualized in 3-D. Colored points represent actual sample determinations. The three bottom axes are True Cotton™ (front axis), Bleached Cotton (right axis), and Polypropylene (rear axis), and the vertical axis indicates R (the time to the onset of clot formation as measured by initial fibrin formation).
Figure 8:
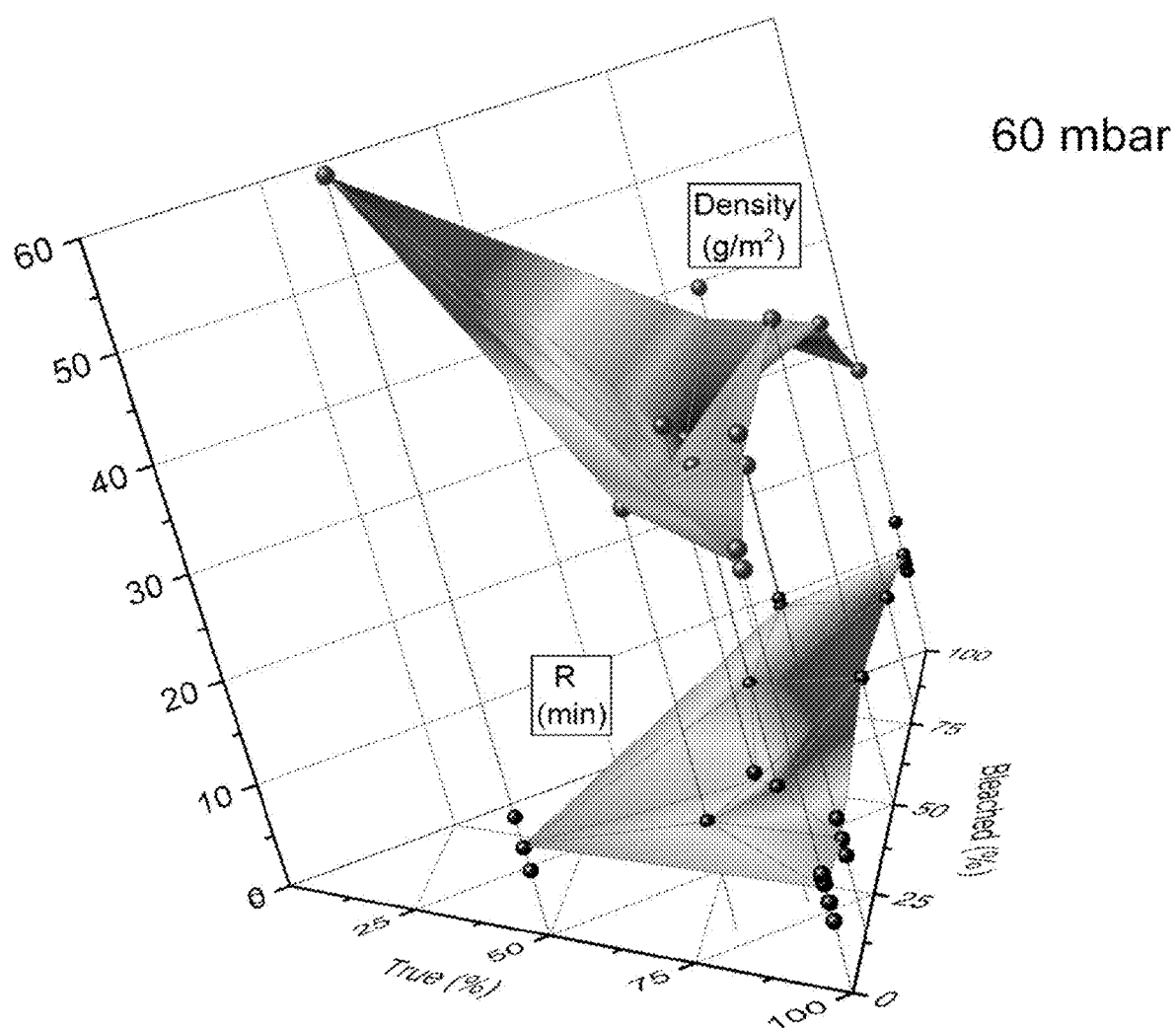
FIG. 8 shows 3-D graphical methods as described below that were employed to identify trends in absorbency (Table 6) that correlate to fabric density (as shown here) and blood clotting properties by varying compositions (i.e., of TC, bleached cotton, and polypropylene) in hydroentangled nonwoven fabrics. The three bottom axes are True Cotton™ (front axis), Bleached Cotton (right axis), and Polypropylene (rear axis). The left back axis is multi-unit (0-20 is minutes, and 20-60 grams per square meter). The lower plate of data shown with a plateau at an R value around 10 mins represents the effect of composition on R (min). Whereas the upper plate peaking at 60 gsm represents the relation of fabric composition and density to R (colored coded by time in minutes to clot formation as shown in FIG. 7A).

Modeling study showing the role of greige cotton in clotting profiles. 3D modeling of a group of Materials versus R: Trends in R values were plotted vs. composition and the results are shown in FIG. 7 for a well-defined data set. A number of approaches were tried to find the best way to use composition or physical properties to predict clotting properties. As shown in FIG. 8, plots of R vs. density of the fabric compositions surprisingly showed an inverse relation between density and R. In FIG. 7, R values were plotted for the materials prepared at 60 mbar. Recall R is the time to the onset of clot formation so low values of R are desired. Surprisingly, the more favorable compositions were thus on the lower left portion of the plot—the green areas nearer the axis for TC, i.e., greige cotton, which was pronounced in FIG. 7 and also present to some extent in FIG. 8. FIG. 8 shows a comparison of the pretreated density and R and their variation with composition. Surprisingly, here it was seen that the inverse relation was found as is highlighted. The results of this analysis confirmed the importance of greige cotton within a larger data set as surprisingly playing an important role in accelerated clotting as determined by individual TEG measurements.

Subsequent to identifying the TEG-based clotting properties, a Lee White clotting assay was employed to demonstrate how the whole materials perform as clotting agents. Surprisingly, trends found with the TEG-based clotting rate determinations were confirmed with the Lee White clotting assay. The following fabrics were tested in the Lee White Clotting Assay:
B10 S-2 (33TC/33bl/33pp) 100b-37.9*,
B10 (50TC/50pp) 60b-65*,
100% TC-60b-35*,
B6 (0TC/100bl/0pp) 60b-27.6*,
UTF 1H*=85TC/15 Tencel,
B1 S-2 (75PA6.6/25TC) 60b-38.2*,
B2 S-2 (15PA6.6/85TC) 60b-38.8*,
B2 (30TC/50bl/20pp) 100b-34.0*,
B7 (100TC/0bl/0pp) 80b-36.6*,
B6S3-50% PA6.6, 50% TC-60 bar-HW, and
B2S3-75% PA6.6, 25% TC-80 bar-LW.

Ascorbic Acid Antimicrobial Finish. Purpose: Treatment of greige cotton-containing material (60/20/20, Greige Cotton/Bleached Cotton/Polypropylene) to impart antimicrobial activity. The padding/ovens used in processing were used to simulate commercial processing. Formulations: Solution 1: 10 mM Ascorbic acid, 1.76 g deionized water (designated house tap), 1 L; Solution 2: 10 mM Sodium ascorbate, 1.98 g, deionized water (designated house tap), 1 L. Machine Settings: Matthis padder: speed 2; 3 padding pressures 5 psi, 15 psi and 30 psi; continuous drying oven(need name): temperature is 85° C.; web run: 0.047 m/min=9 min 56 sec; samples were 25 inL×4 in W→62.5 cm×10.2 cm→0.62 m. Data shown in the tables below:

| | Fabric Data | | | |
|---|---|---|---|---|
| Sample ID | Sample Description | Before wt (g) | Wet padded wt (g) | After wt.(g) |
| 062118-1 | 5 psi 10 mM Ascorbic acid | 4.51 | 14.04 | 4.52 |
| 062118-2 | 5 psi 10 mM Ascorbic acid | 4.41 | 13.92 | 4.40 |
| 062118-3 | 15 psi 10 mM Ascorbic acid | 4.57 | 14.51 | 4.59 |
| 062118-4 | 15 psi 10 mM Ascorbic acid | 4.47 | 14.09 | 4.47 |
| 062118-5 | 30 psi 10 mM Ascorbic acid | 4.75 | 20.06 | 4.77 |
| 062118-6 | 30 psi 10 mM Ascorbic acid | 4.72 | 12.05 | 4.73 |
| 062118-7 | 5 psi 10 mM Sodium Ascorbate | 4.79 | 26.33 | 4.85 |
| 062118-8 | 5 psi 10 mM Sodium Ascorbate | 4.86 | 26.25 | 4.92 |
| 062118-9 | 15 psi 10 mM Sodium Ascorbate | 4.75 | 14.71 | 4.77 |
| 062118-10 | 15 psi 10 mM Sodium Ascorbate | 4.70 | 14.62 | 4.72 |
| 062118-11 | 30 psi 10 mM Sodium Ascorbate | 4.90 | 15.35 | 4.92 |
| 062118-12 | 30 psi 10 mM Sodium Ascorbate | 4.78 | 14.89 | 4.81 |

| | Fabric Results | | |
|---|---|---|---|
| Sample ID | Sample Description | Wet kickup % | % Add-On |
| 062118-1 | 5 psi 10 mM Ascorbic acid | 211.31 | 0.22 |
| 062118-2 | 5 psi 10 mM Ascorbic acid | 215.65 | −0.23 |
| 062118-3 | 15 psi 10 mM Ascorbic acid | 217.51 | 0.44 |
| 062118-4 | 15 psi 10 mM Ascorbic acid | 215.21 | 0.00 |
| 062118-5 | 30 psi 10 mM Ascorbic acid | 322.32 | 0.42 |
| 062118-6 | 30 psi 10 mM Ascorbic acid | 155.30 | 0.21 |
| 062118-7 | 5 psi 10 mM Sodium Ascorbate | 449.69 | 1.25 |
| 062118-8 | 5 psi 10 mM Sodium Ascorbate | 440.12 | 1.23 |
| 062118-9 | 15 psi 10 mM Sodium Ascorbate | 209.68 | 0.42 |
| 062118-10 | 15 psi 10 mM Sodium Ascorbate | 211.06 | 0.43 |
| 062118-11 | 30 psi 10 mM Sodium Ascorbate | 213.27 | 0.41 |
| 062118-12 | 30 psi 10 mM Sodium Ascorbate | 211.51 | 0.63 |

The samples below were treated as before in our lab, same solution, submerged, squeeze/hand blot and dried at 85° C. in force draft oven without tension. This time, it was weighed for wet pick up calculation. The data is shown in the table below.

| Sample ID | Sample Description | before | Wet blot | after | Wet pick up % | % add-on |
|---|---|---|---|---|---|---|
| 062618-1A | 10 mM Ascorbic acid | 2.2896 | 17.28 | 2.29 | 654.72 | 0.02 |
| 062618-1B | 10 mM Ascorbic acid | 2.2829 | 16.96 | 2.28 | 642.91 | −0.13 |
| 062618-2A | 10 mM Sodium Ascorbate | 2.3130 | 17.40 | 2.3423 | 652.27 | 1.27 |
| 062618-2B | 10 mM Sodium Ascorbate | 2.3156 | 16.82 | 2.3459 | 626.38 | 1.31 |

Selected fabrics were submitted to Situbiosciences (Wheeling, Ill.) for fabric testing, AATCC TM 100 test method designed to measure the antimicrobial properties of textile or absorbent material incubated with selected microorganisms. These samples were tested against K. pneumoniae (4352) and S. aureus (6538). At time 0, the bacterial levels were $7.6 \times 10^4$ CFU/mL and $5.3 \times 10^5$ CFU/mL for K. pneumoniae and S. aureus respectively. Their levels at 24 hrs are noted in table below. Sample #4 was retested and no change in result, ineffective against these bacteria.

| | | AATCC 100 TM | |
|---|---|---|---|
| # | Sample ID | Sample Description | % reduction after 24 hrs |
| 1 | 062118-1 | 5 psi 10 mM Ascorbic acid | 99.99/99.99 |
| 2 | 062118-5 | 30 psi 10 mM Ascorbic acid | 99.35/99.99 |
| 3 | 062118-7 | 5 psi 10 mM Sodium Ascorbate | 99.95/95.09 |
| 4 | 062118-12 | 30 psi 10 mM sodium Ascorbate | 0/0 |
| 5 | 062618-1A-B | 10 mM Ascorbic acid(NTP ctrl) | 99.99/99.99 |
| 6 | 062118-3 | Untreated HEM Gauze ctrl | 0/72.47 |
| 7 | Situ lab ctrl | *K. pneumoniae/S aureus* | 8.2E6/3.0E6 CFU/mL |

Figure 2:
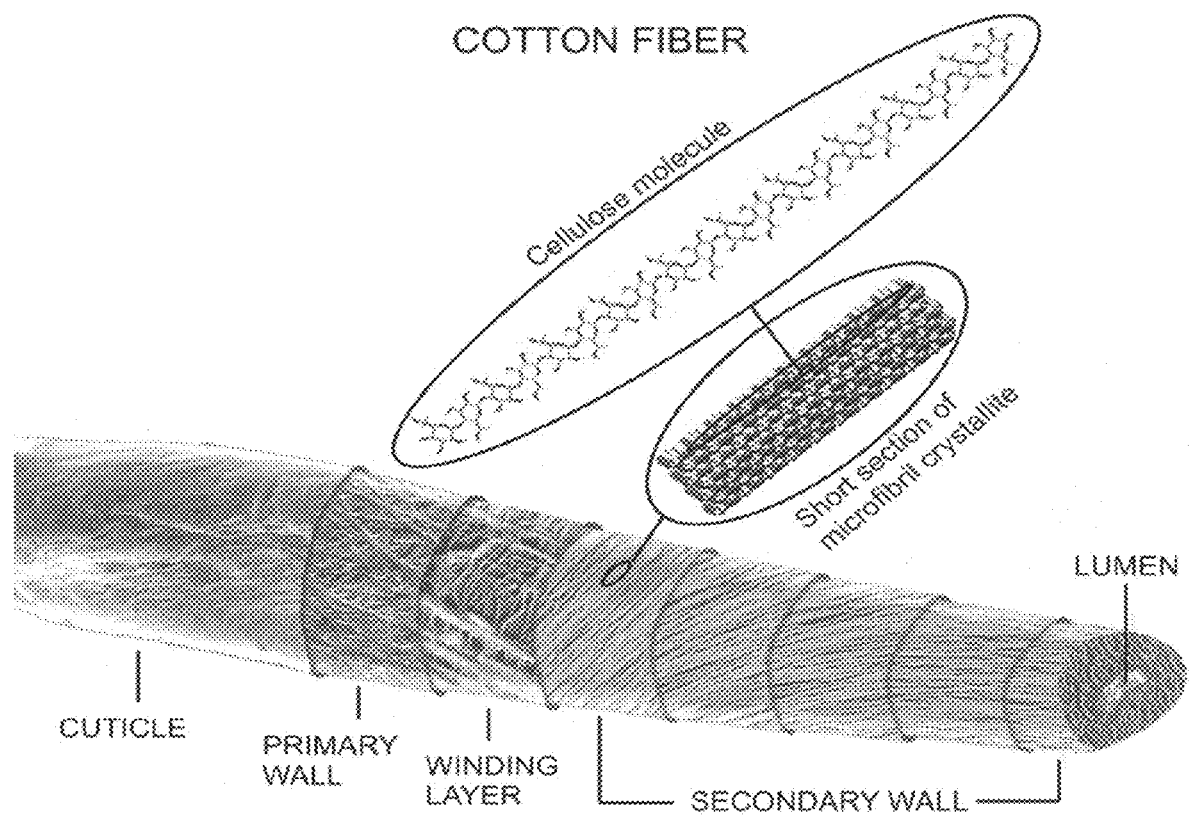
FIG. 2 shows a diagram of unbleached cotton fiber. The outer layer, consisting of the cuticle and primary cell wall, contains waxes and pectin which are not retained upon bleaching and scouring; the other layers portrayed consist of cellulose I that is assembled into microfibril sections that constitute the principle structure of the cotton fiber as described below.

Multilayered Dressing Design: One specific dressing design incorporated the fiber features illustrated in FIG. 2 where the detailed structure of cotton fiber components are depicted. A description of the multilayered samples is outlined in Table 9. This part of the study defined a layered motif with either two or three distinct nonwoven layers with the outside layers having the same blend of more hydrophilic fibers (e.g., bleached cotton, tencel, viscose) (see FIG. 3) and the inside layer having a different blend of more hydrophobic fibers (e.g., polypropylene, nylon, and forms of TC). The outside layers in the 'sandwich design' portrayed in FIG. 3 surprisingly have a high absorption capacity and wicking functionality and contain a fiber blend that is good at promoting clot formation. The inner layer contains a more hydrophobic component which when combined with the outer layer is designed to enable enhanced uptake and retention of blood by a mechanism that employs the juxtaposition of a hydrophobic material with a hydrophilic material. Both enhanced absorption capacity and wicking improved uptake and retention of blood in the material which in turn enable clot formation. Thus, increasing the hydrophobicity of the material can improve the absorption capacity and increasing hydrophilicity improves wicking, surprisingly the combination of these in an amphiphilic design improves clotting potentiation through rapid uptake and prolonged retention of clotted blood. The use of these materials in a 'sandwich design' was shown to have a synergistic effect by promoting more rapid strikethrough and wicking and high absorption capacity with very good fiber-based blood clot acceleration. These properties were tested as discussed below using thromboelastography of the constituent fibers, absorption capacity, wicking of the materials, and electrokinetic assessment to define relative polarity of the singular layers. A depiction of the ability of the multi-layered dressing to rapidly wick physiological saline and achieve high absorption capacities is demonstrated in FIG. 10 and FIG. 9 respectively. For example, as show in FIG. 10, increasing the amount of hydrophilic bleached cotton surprisingly increased the uptake of saline solution 4-fold in multilayered dressings. On the other hand, absorption capacity was found to surprisingly increase as a function of a hydrophilic outer layers and a more hydrophobic inner layer.

All of the references cited herein, including U.S. Patents and U.S. Patent Application Publications, are incorporated by reference in their entirety. Also incorporated by reference in their entirety are the following references: Wagner, W., et al., J. Surgical Res., 66: 100-108 (1996); U.S. Pat. Nos. 6,809,231; 9,474,827; 9,463,119; U.S. Patent Application Publication Number 20170128270.

Thus, in view of the above, there is described (in part) the following:

A single layered nonwoven wound dressing comprising (or consisting essentially of or consisting of) about 5% by weight to about 95% by weight non-scoured, non-bleached greige cotton fibers, about 5% by weight to about 95% by weight bleached cotton fibers, and about 5% by weight to about 60% by weight hydrophobic fibers, all percentages adding up to 100 wt %. The above single layered nonwoven wound dressing, wherein said dressing comprising (or consisting essentially of or consisting of) about 30% by weight non-scoured, non-bleached greige cotton fibers, about 50% by weight bleached cotton fibers, and about 20% by weight hydrophobic fibers. The above single layered nonwoven wound dressing, wherein said hydrophobic fibers are selected from the group consisting of polypropylene, nylon, and mixtures thereof. The above single layered nonwoven wound dressing, wherein said non-scoured, non-bleached greige cotton has a purity level of about 99.9%. The above single layered nonwoven wound dressing, wherein said dressing further comprises kaolin and pectin, wherein said pectin adheres said kaolin to said fibers. The above single layered nonwoven wound dressing, wherein said nonwoven wound dressing is produced by a process comprising (or consisting essentially of or consisting of):

(a) preparing needle punched webs of the fibers, (b) uniformly hydroentangling said webs using a system (e.g., Fleissner MiniJet system) wherein said system is equipped with one low water pressure (e.g., about 30 bars) jet head that wets said webs on the top face of said webs to form a wetted substrate and wherein said system is equipped with two high water pressure (e.g., about 60 to about 100 bars) jet heads that subsequently alternatively wets said wetted substrate on either face of said wetted substrate, wherein said system utilizes an about 23 mesh to about 17 mesh screen, and (c) drying said wetted substrate to form said dressing.

A single layered nonwoven wound dressing comprising (or consisting essentially of or consisting of) about 5% by weight to about 95% by weight non-scoured, non-bleached greige cotton fibers, about 5% by weight to about 95% by weight bleached cotton fibers, and about 5% by weight to about 60% by weight hydrophobic fibers, all percentages adding up to 100 wt %, wherein said nonwoven wound dressing is produced by a process comprising (or consisting essentially of or consisting of):

(a) preparing needle punched webs of the fibers, (b) uniformly hydroentangling said webs using a system (e.g., Fleissner MiniJet system) wherein said system is equipped with one low water pressure (e.g., about 30 bars) jet head that wets said webs on the top face of said webs to form a wetted substrate and wherein said system is equipped with two high water pressure (e.g., about 60 to about 100 bars) jet heads that subsequently alternatively wets said wetted substrate on either face of said wetted substrate, wherein said system utilizes an about 23 mesh to about 17 mesh screen, and (c) drying said wetted substrate to form said dressing.

A multi-layered nonwoven wound dressing, comprising (or consisting essentially of or consisting of) at least one inner layer containing about 50% by weight to about 95% by weight non-scoured, non-bleached greige cotton fibers and about 5% by weight to about 50% by weight hydrophobic fibers, all percentages adding up to 100 wt %, and at least one outer layer containing about 5% by weight to about 95% by weight non-scoured, non-bleached greige cotton fibers, about 5% by weight to about 95% by weight bleached cotton fibers, and about 5% by weight to about 60% by weight hydrophobic fibers, all percentages adding up to 100 wt % (e.g., 30TC/50bl/20pp).

A nonwoven wound dressing, comprising (or consisting essentially of or consisting of): (a) a first layer, wherein the first layer contains about 50% by weight to about 95% by weight non-scoured, non-bleached greige cotton fibers and about 5% by weight to about 50% by weight hydrophobic fibers (e.g., polypropylene, nylon), all percentages adding up to 100 wt %; and (b) a second layer, wherein the second layer contains about 5% by weight to about 95% by weight non-scoured, non-bleached greige cotton fibers, about 5% by weight to about 95% by weight bleached cotton fibers, and about 5% by weight to about 60% by weight hydrophobic fibers, all percentages adding up to 100 wt % (e.g., 30TC/50bl/20pp).

The term "consisting essentially of" excludes additional method (or process) steps or composition components that substantially interfere with the intended activity of the method (or process) or composition, and can be readily determined by those skilled in the art (for example, from a consideration of this specification or practice of the invention disclosed herein).

The invention illustratively disclosed herein suitably may be practiced in the absence of any element (e.g., method (or process) steps or composition components) which is not specifically disclosed herein. Thus the specification includes disclosure by silence ("Negative Limitations In Patent Claims," AIPLA Quarterly Journal, Tom Brody, 41(1): 46-47 (2013): " . . . Written support for a negative limitation may also be argued through the absence of the excluded element in the specification, known as disclosure by silence . . . Silence in the specification may be used to establish written description support for a negative limitation. As an example, in Ex parte Lin [No. 2009-0486, at 2, 6 (B.P.A.I. May 7, 2009)] the negative limitation was added by amendment . . . In other words, the inventor argued an example that passively complied with the requirements of the negative limitation . . . was sufficient to provide support . . . This case shows that written description support for a negative limitation can be found by one or more disclosures of an embodiment that obeys what is required by the negative limitation. . . . "

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

TABLE 1

Results of initial study utilizing samples containing greige cotton and Tencel:

|  | R | StDev | k | StDev | Angle | StDev | MA | StDev |
|---|---|---|---|---|---|---|---|---|
| Combat Gauze | 2.4 | 0.1 | 1.1 | 0.3 | 70.0 | 8.9 | 70.2 | 0.1 |
| UT-F-1H | 4.1 | 0.6 | 3.8 | 1.0 | 47.1 | 7.0 | 69.3 | 1.2 |
| UT-24-1L | 4.6 | 0.5 | 3.9 | 1.5 | 43.8 | 12.6 | 61.9 | 6.4 |
| Rayon/Poly | 4.8 | 0.5 | 4.2 | 0.1 | 42.1 | 1.7 | 64.2 | 0.6 |
| Sample V | 4.8 | 1.2 | 4.6 | 1.5 | 37.2 | 2.4 | 50.5 | 3.7 |
| Sample VIII | 4.7 | 0.3 | 5.0 | 0.4 | 37.4 | 1.4 | 67.8 | 0.1 |
| UT-24-2L | 5.1 | 0.6 | 4.7 | 0.7 | 42.8 | 6.0 | 58.1 | 0.1 |
| UT-FM-2L | 5.6 | 0.2 | 4.6 | 0.4 | 34.8 | 0.5 | 49.4 | 0.2 |
| 100% Greige Cotton | 5.9 | 1.1 | 4.5 | 0.9 | 38.7 | 5.5 | 47.0 | 1.6 |
| UT-F-2L | 5.9 | 0.3 | 6.4 | 0.4 | 30.8 | 0.8 | 45.2 | 1.1 |
| UT-F-2H | 6.9 | 0.9 | 5.1 | 0.2 | 38.6 | 1.3 | 50.2 | 1.2 |
| UT-24-3L | 7.0 | 0.8 | 4.7 | 1.7 | 37.8 | 7.7 | 45.7 | 0.3 |
| Bovine Blood | 14.5 | 2.5 | 5.3 | 2.1 | 32.5 | 6.9 | 58.2 | 10.8 |
| Bovine Blood | 10.5 | 2.5 | 4.8 | 1.6 | 29.7 | 4.3 | 45.3 | 1.5 |

TABLE 2

Composition of above samples
Composition of Material of initial study

| Combat Gauze | Comp. and Blend Ratio Rayon/Polyester + Kaolin | | Mesh or Pattern | Wgt. |
|---|---|---|---|---|
| UT-F-1H | Tencel 15 | GC 85 | 22 × 23 | 55 |
| UT-24-1L | Tencel 15 | GC 85 | 22 × 23 | 45 |
| Rayon/Poly | rayon 70 | PES 30 | fine aperture |  |
| Sample V | viscose 50 | GC 50 | fine aperture |  |
| Sample VIII | 50 PP | GC 50 | fine aperture | 25 |
| UT-24-2L | Tencel 25 | GC 75 | 22 × 23 | 45 |
| UT-FM-2L | Tencel 25 | GC 75 | 55LD | 45 |
| 100% Greige Cotton |  | GC 100 | no pattern | 45 |
| UT-F-2L | Tencel 25 | GC 75 | 103A | 45 |
| UT-F-2H | Tencel 25 | GC 75 | 103A | 55 |
| UT-24-3L | Tencel 50 | GC 50 | 22 × 23 | 45 |

GC = greige cotton (True Cotton),
PP = polypropylene

TABLE 3

TEG Summary of TEG results varying composition ratio TC/Bl/PP.

| | | | | | | | | | |
|---|---|---|---|---|---|---|---|---|---|
| 100TC 35 g/m2 80 b | Jan. 25, 2016 | 8.5 | 0.4 | 3.6 | 0.6 | 29.7 | 0.3 | 49 | 5.3 |
| bovine blood | Jan. 27, 2016 | 11.8 | 1.9 | 7.6 | 1.5 | 23.2 | 9.3 | 53.5 | 7.5 |
| B6 (0T/100bl/0pp) 60 b - 27.6* | Jan. 27, 2016 | 8 | 0.3 | 4 | 0.8 | 29.4 | 1.3 | 58.2 | 1.8 |
| bovine blood | Feb. 1, 2016 | 14.6 | 0.6 | 5.5 | 0.3 | 29 | 0.8 | 44.2 | 4.5 |
| B8 (0T/80bl/20pp) 80 b - 39.5* | Feb. 1, 2016 | 6.8 | 0.1 | 5.2 | 0.6 | 25.8 | 2.1 | 48.3 | 1.1 |
| bovine blood | Jan. 27, 2016 | 11.8 | 1.9 | 7.6 | 1.5 | 23.2 | 9.3 | 53.5 | 7.5 |
| B6 (0T/100bl/0pp) 60 b - 27.6* | Jan. 27, 2016 | 8 | 0.3 | 4 | 0.8 | 29.4 | 1.3 | 58.2 | 1.8 |
| blood bovine (B-B6063) | Apr. 20, 2016 | 11.8 | 0.6 | 5.6 | 0.4 | 35.1 | 0 | 62.2 | 2 |
| B7 (100TC/0bl/0pp) 80 b - 36.6* | Apr. 19, 2015 | 7.6 | 0.6 | 3.6 | 0.4 | 38.9 | 9.9 | 66.2 | 3.9 |
| bovine blood (B-B6063) | Apr. 21, 2016 | 13.8 | 0.4 | 5 | 0.3 | 32.6 | 3.5 | 62.4 | 1 |
| B1 (85TC/15bl/0pp) 60 b - 41.9 | Apr. 21, 2016 | 6.8 | 0.4 | 5.8 | 0.4 | 27.4 | 1.9 | 57.6 | 7.9 |
| B2 (30TC/50bl/20pp) 100 b - 34.0* | Apr. 22, 2016 | 9.3 | 1 | 3.8 | 0.3 | 40.1 | 2.4 | 57.3 | 1.5 |
| blood, bovine | Jul. 11, 2016 | 12.3 | 0.7 | 4.4 | 0.1 | 35.4 | 7.7 | 39.2 | 0.9 |
| B4 S-2 (30% TC, 50% bl/20% pp) 60 b - 39.0 | Jul. 12, 2016 | 11.9 | 1.2 | 6.7 | 2.5 | 20.9 | 1.6 | 37.3 | 1.6 |
| blood, bovine | Jul. 15, 2016 | 12.3 | 0.4 | 5.3 | 0.2 | 21.3 | 11.5 | 29.6 | 2.3 |
| B10 S-2 (33TC/33bl/33pp) 100 b - 37.9 | Jul. 15, 2016 | 10.8 | 0.5 | 4.6 | 1.1 | 29.4 | 15.5 | 31.6 | 0.1 |
| blood, bovine | Jul. 20, 2016 | 15 | 1.7 | 7 | 1.7 | 29.8 | 4.7 | 67.4 | 1.7 |
| B1 S-2 (75PA6.6/25TC) 60 b - 38.2* | Jul. 20, 2016 | 10.9 | 0.3 | 6.4 | 0.1 | 33.8 | 0 | 68.6 | 1.1 |
| bovine blood | Dec. 4, 2015 | 9.4 | 0.9 | 4.6 | 0.8 | 35.8 | 4.2 | 34.3 | 3.3 |
| UTF 1H* | Dec. 4, 2015 | 6.5 | 0.4 | 3.2 | 0.1 | 34.1 | 0.8 | 44.2 | 0.8 |
| 85 TC 15 Tencel bovine blood | Dec. 22, 2015 | 16.8 | 1.4 | 6.4 | 0.6 | 22 | 8.3 | 35.8 | 4.5 |
| UT F 1H Pectin and kaolin | Dec. 22, 2015 | 7 | 0.9 | 3.4 | 1.7 | 36.5 | 15.7 | 33.6 | 1.2 |
| bovine blood | Jan. 27, 2016 | 11.8 | 1.9 | 7.6 | 1.5 | 23.2 | 9.3 | 53.5 | 7.5 |
| B6 (0T/100bl/0pp) 60 b - 27.6* | Jan. 27, 2016 | 8 | 0.3 | 4 | 0.8 | 29.4 | 1.3 | 58.2 | 1.8 |
| bovine blood | Feb. 1, 2016 | 14.6 | 0.6 | 5.5 | 0.3 | 29 | 0.8 | 44.2 | 4.5 |

TABLE 4 electrokinetic Results For Fiber Combinations:

| Sample | ☐plateau | Δζ* | $R^2$ | $\zeta_0$ | $\zeta_\infty$ | Swell Ratio |
|---|---|---|---|---|---|---|
| B1 (85TC/15bl/0pp) 60 b - 41.9 | −31 | 0.14 | 0.902 | −32.58 | −29.76 | 1.05 |
| B1 (85TC/15bl/0pp) 60 b - 39.4 | −29 | 0.07 | 0.83 | −30.58 | −28.00 | 1.05 |
| B2 (30TC/50bl/20pp) 60 b - 32.5 | −36 | 0.09 | 0.84 | −34.60 | −32.44 | 1.03 |
| B2 (30TC/50bl/20pp) 60 b - 34.0 | −37 | 0.09 | 0.946 | −40.62 | −37.18 | 1.04 |
| B3 (70TC/10bl/20pp) 60 b - 36.5 | −35 | 0.09 | 0.97 | −36.80 | −33.72 | 1.04 |
| B3 (70TC/10bl/20pp) 60 b - 37.8 | −37 | 0.06 | 0.948 | −40.43 | −38.17 | 1.03 |
| B4 (60TC/25bl/15pp) 60 b - 34.0 | −38 | 0.06 | 0.941 | −39.62 | −37.17 | 1.03 |
| B4 (60TC/25bl/15pp) 60 b - 39.8 | −30 | 0.10 | 0.97 | −30.19 | −27.08 | 1.06 |
| B5 (20TC/50bl/0pp) 60 b - 36.4 | −27 | 0.07 | 0.98 | −24.94 | −23.28 | 1.04 |
| B5 (20TC/50bl/0pp) 60 b - 42.2 | −30 | 0.06 | 0.944 | −32.02 | −29.96 | 1.03 |
| B6 (0TC/100bl/0pp) 60 b - 27.6 | −25 | 0.09 | 0.99 | −23.43 | −21.51 | 1.04 |
| B6 (0TC/100bl/0pp) 60 b - 37.3 No 60b for this sample | −32 | 0.046 | 0.939 | −32.99 | −31.27 | 1.03 |
| B7 (100TC/0bl/0pp) 60 b - 36.6 | −31 | 0.05 | 0.45 | −31.61 | −30.63 | 1.02 |
| B8 (0TC/80bl/20pp) 60 b - 39.5 | −37 | 0.08 | 0.96 | −34.63 | −32.11 | 1.04 |
| B8 (0TC/80bl/20pp) 60 b - 30.8 | −41 | 0.046 | 0.881 | −40.88 | −38.96 | 1.02 |
| B9 (50TC/50bl/0pp) 60 b - 43.3 | −28 | 0.06 | 0.91 | −29.72 | −27.53 | 1.04 |
| B9 (50TC/50bl/0pp) 60 b - 45.0 | −31 | 0.09 | 0.95 | −32.58 | −29.76 | 1.04 |
| B10 (50TC/0bl/50pp) 60 b - 65 | −48 | 0.08 | 0.96 | −48.71 | −44.94 | 1.04 |

| Nylon-Containing Samples | | | ☐plateau | Δζ** | $R^2$ | $\zeta_0$ | $\zeta_\infty$ | Swell Ratio |
|---|---|---|---|---|---|---|---|---|
| Nylon | | | −69 | 0.2 | 0.98 | −85.5 | −67.5 | 1.12 |
| B1 S-2 | 75% PA6.6/25% TC | 38.2 g/m2 | −58 | 0.20 | 0.98 | −74.57 | −66.01 | 1.06 |
| B2 S-2 | 15% PA6.6/85% TC | 38.8 g/m2 | −33 | 0.99 | 0.90 | −33.50 | −32.44 | 1.02 |

TABLE 4-continued electrokinetic Results For Fiber Combinations:

| B3 S-2 | 70% TC/20% bl/10% pp | 36.7 g/m2 | −33 | 0.06 | 0.95 | −34.66 | −32.66 | 1.03 |
| B4 S-2 | 30% TC/50% bl/20% pp | 39.0 g/m2 | −38 | 0.07 | 0.95 | −39.09 | −36.60 | 1.03 |
| B5 S-3 | 85% TC/15% bl/0% pp | 35.3 g/m2 | −29.5 | 0.77 | 0.98 | −29.53 | −27.35 | 1.04 |
| B6 S-2 | 50% TC/0% bl/50% pp | 36.7 g/m2 | −40 | 0.09 | 0.95 | −50.83 | −46.57 | 1.04 |
| B7 S-2 | 0% TC/80% bl/20% pp | 36.5 g/m2 | −35 | −0.07 | 0.97 | −35.01 | −33.51 | 1.02 |
| B8 S-2 | 0% TC/100% bl/0% pp | 34.0 g/m2 | −26 | 0.05 | 0.94 | −26.03 | −24.78 | 1.02 |
| B9 S-2 | 100% TC/0% bl/0% pp | 38.9 g/m2 | −32.5 | 0.06 | 0.86 | −31.56 | −30.12 | 1.02 |
| B10 S-2 | 33% TC/33% bl/33% pp | 36.9 g/m2 | −40 | 0.05 | 0.91 | −43.61 | −41.65 | 1.02 |

TABLE 5a

TEG results for Nylon-Containing Samples

| Sample | R min | Stdev | k min | Stdev | angle deg | stdev | MA mm | stdev |
|---|---|---|---|---|---|---|---|---|
| bovine blood - 6738 | 11.6 | 0.1 | 4.1 | 0.1 | 32.0 | 10.0 | 53.0 | 2.9 |
| B1S3-100% PA6.6-60 bar-LW | 11.7 | 1.2 | 5.8 | 0.9 | 24.3 | 6.2 | 41.9 | 2.8 |
| B2S3-75% PA6.6, 25% TC-60 bar-LW | 8.6 | 2.0 | 4.2 | 0.9 | 29.1 | 3.1 | 51.7 | 3.6 |
| B9S3-10% PA6.6, 90% bl 60 bar | 10.2 | 0.2 | 3.7 | 0.1 | 42.2 | 1.6 | 56.8 | 3.9 |
| bovine blood | 12.4 | 1.4 | 6.5 | 1.7 | 26.8 | 8.7 | 49.7 | 4.7 |
| B1S3-100% PA6.6-810.60 bar-LW | 10.6 | 0.5 | 7.1 | 0.7 | 26.2 | 3.7 | 45.8 | 2.9 |
| B2S3-75% PA6.6, 25% TC-80 bar-LW | 8.4 | 0.2 | 6.6 | 1.7 | 23.6 | 1.5 | 47.6 | 2.0 |
| bovine blood - 7242 | 21.7 | 2.7 | 12.9 | 2.1 | 19.7 | 2.7 | 64.8 | 1.7 |
| combat gauze | 4.3 | 1.1 | 1.2 | 0.3 | 60.6 | 11.2 | 65.4 | 4.0 |
| B7S3-50% PA6.6, 50% bl-80 bar-LW | 8.7 | 2.2 | 5.0 | 1.0 | 36.2 | 6.2 | 63.3 | 3.0 |
| B8S3-85% PA6.6, 15% bl-80 bar-LW | 11.5 | 0.4 | 5.9 | 0.4 | 31.0 | 5.9 | 63.2 | 4.6 |
| B9S3-10% PA6.6, 90% bl-80 bar | 8.0 | 0.5 | 3.0 | 0.6 | 42.8 | 4.1 | 64.0 | 8.8 |
| bovine blood | 16.8 | 1.5 | 9.2 | 0.8 | 25.1 | 2.1 | 63.0 | 2.8 |

TABLE 5b

Electrokinetic Profile of samples show in Table 5a

| | Plateau Potenti | Δζ** | $R^2$ | $\zeta_0$ | $\zeta_\infty$ | Swell Ratio |
|---|---|---|---|---|---|---|
| B1S3-100% PA6.6-60 bar-LW | −80 | 0.191 | 0.988 | −99.54 | −84.49 | 1.09 |
| B2S3-75% PA6.6, 25% TC-60 bar-LW | −65 | 0.079 | 0.972 | −74.10 | −69.00 | 1.04 |
| B3S3-15% PA6.6, 85% TC-60 bar-LW | −27 | 0.070 | 0.968 | −28.16 | −26.74 | 1.03 |
| B4S3-20% PA6.6, 30% TC, 50% bl-60 bar-LW | −26 | 0.103 | 0.985 | −28.16 | −25.36 | 1.05 |
| B5S3-33.3% PA6.6, 33.3% TC, 33.3% bl-60 bar-LW | −28 | 0.190 | 0.992 | −35.40 | −29.41 | 1.10 |
| B6S3-50% PA6.6, 50% TC, -60 bar-LW | −39 | 0.121 | 0.976 | −47.30 | −42.08 | 1.06 |
| B7S3-50% PA6.6, 50% bl-60 bar-LW | −39 | 0.095 | 0.983 | −43.34 | −39.40 | 1.05 |
| B8S3-85% PA6.6, 15% bl-60 bar-LW | −55 | 0.225 | 0.980 | −64.20 | −51.28 | 1.12 |
| B9S3-10% PA6.6, 90% bl-60 bar-LW | −23 | 0.071 | 0.863 | −27.49 | −25.23 | 1.04 |

TABLE 6

Absorption Capacity of TC/BL/PP

| Sample | # Runs | SA mg/cm² | Abs Cap (g/g) |
|---|---|---|---|
| B1 (85TC/15bl/0pp) 60b - 41.9 | 1 | 2.7 | 15.34 |
| B1 (85TC/15bl/0pp) 80b - 41.9 | 1 | 3.25 | 12.51 |
| B1 (85TC/15bl/0pp) 100b - 41.9 | 1 | 4.01 | 12.12 |
| B1 (85TC/15bl/0pp) 60b-39.4 | 1 | 3.9 | 14.35 |
| B1 (85TC/15bl/0pp) 80b-39.4 | 1 | 3.8 | 13.583 |
| B1 (85TC/15bl/0pp) 100b - 39.4 | 1 | 2.94 | 13.56 |
| B2 (30TC/50bl/20pp) 60b - 34.0 | 1 | 3.2 | 17.88 |
| B2 (30TC/50bl/20pp) 80b - 34.0 | 1 | 2.14 | 15.74 |
| B2 (30TC/50bl/20pp) 100b - 34.0 | 1 | 2.86 | 16.86 |
| B2 (30TC/50bl/20pp) 60b - 32.5 | 1 | 2.42 | 14.67 |
| B2 (30TC/50bl/20pp) 80b - 32.5 | 1 | 2.85 | 14.09 |
| B2 (30TC/50bl/20pp) 100b - 32.5 | 1 | 3.14 | 14.51 |
| B3 (70TC/10bl/20pp) 60b - 36.5 | 1 | 2.00 | 12.90 |
| B3 (70TC/10bl/20pp) 80b - 36.5 | 1 | 1.94 | 12.86 |
| B3 (70TC/10bl/20pp) 100b - 36.5 | 1 | 1.93 | 12.50 |
| B3 (70TC/10bl/20pp) 60b-37.8 | 1 | 3.4 | 13.14 |
| B3 (70TC/10bl/20pp) 80b-37.8 | 1 | 3.4 | 13.55 |
| B3 (70TC/10bl/20pp) 100b - 37.8 | 1 | 2.60 | 13.18 |
| B4 (60TC/25bl/15pp) 60b-39.8 | 1 | 4.1 | 14.41 |
| B4 (60TC/25bl/15pp) 80b-39.8 | 1 | 4.2 | 15.27 |
| B4 (60TC/25bl/15pp) 100b - 39.8 | 1 | 2.00 | 14.53 |
| B4 (60TC/25bl/15pp) 600b - 34.0 | 1 | 2.89 | 16.69 |
| B4 (60TC/25bl/15pp) 80b - 34.0 | 1 | 2.86 | 14.92 |
| B4 (60TC/25bl/15pp) 100b - 34.0 | 1 | 3.73 | 14.71 |
| B6 (0TC/100bl/0pp) 60b - 27.6 | 1 | 2.7 | 16.58 |
| B6 (0TC/100bl/0pp) 80b - 27.6 | 1 | 2.8 | 16 |
| B6 (0TC/100bl/0pp) 100b - 27.6 | 1 | 3.12 | 16.71 |
| B6 (0TC/100bl/0pp) 60b - 37.3 | 1 | 4.67 | 16.88 |
| B6 (0TC/100bl/0pp) 80b - 37.3 | 1 | 2.08 | 17.11 |
| B6 (0TC/100bl/0pp) 100b - 37.3 | 1 | 2.80 | 16.71 |
| B7 (100TC/0bl/0pp) 60b - 36.6 | 1 | 3.15 | 12.28 |
| B7 (100TC/0bl/0pp) 80b - 36.6 | 1 | 3.17 | 13.59 |
| B7 (100TC/0bl/0pp) 100b - 36.6 | 1 | 3.26 | 12.95 |
| No 60b for this sample | 1 | | |
| B7 (100TC/0bl/0pp) 80b - 41.0 | 1 | 2.57 | 11.16 |
| B7 (100TC/0bl/0pp) 100b - 41.0 | 1 | 3.50 | 12.77 |
| B8 (0TC/80bl/20pp) 60b - 39.5 | 1 | 3.6 | 14.60 |
| B8 (0TC/80bl/20pp) 80b - 39.5 | 1 | 3.6 | 14.99 |
| B8 (0TC/80bl/20pp) 100b -39.5 | 1 | 3.15 | 13.34 |
| B8 (0TC/80bl/20pp) 60b -30.8 | 1 | 7.58 | 14.87 |
| B8 (0TC/80bl/20pp) 80b - 30.8 | 1 | 2.81 | 13.64 |
| B8 (0TC/80bl/20pp) 100b - 30.8 | 1 | 2.80 | 13.79 |
| B9 (50TC/50bl/0pp) 60b - 43.3 | 1 | 3.00 | 15.48 |
| B9 (50TC/50bl/0pp) 80b - 43.3 | 1 | 2.68 | 13.61 |
| B9 (50TC/50bl/0pp) 100b - 43.3 | 1 | 3.64 | 13.13 |
| B9 (50TC/50bl/0pp)60b - 45 | 1 | 3.02 | 15.55 |
| B9 (50TC/50bl/0pp)80b - 45 | 1 | 2.73 | 13.51 |
| B9 (50TC/50bl/0pp)100b - 45 | 1 | 3.30 | 13.18 |
| B10 (50TC/0bl/50pp) 60b - 65 | 1 | 1.76 | 1.97 |
| B10 (50TC/0bl/50pp) 80b - 65 | 1 | 1.50 | 4.29 |
| B10 (50TC/0bl/50pp) 100b - 65 | 1 | 1.40 | 6.08 |
| No 60b for this sample | | | |
| B10 (50TC/0bl/50pp) 80b - 66 | 1 | 1.76 | 2.28 |
| B10 (50TC/0bl/50pp) 100b - 66 | 1 | 1.48 | 2.63 |
| Kerlix | 2 | 9.71 | 5.45 |
| Combat Gauze | 2 | 4.40 | 9.48 |
| Rayon/Polyester | 2 | 3.80 | 16.2 |
| 50% TC/50% pp | 3 | 2.28 | 3.57 |
| #6 | 4 | 1.45 | 3.48 |
| B1 S-2 (75% PA6.6/25% TC) 60b - 38.2 | 1 | 9.27 | 12.08 |
| B1 S-2 (75% PA6.6/25% TC) 80b - 45.0 | 1 | 6.3 | 12.27 |
| B1 S-2 (75% PA6.6/25% TC) 100b - 45.0 | 1 | 2.3 | 10.45 |
| B2 S-2 (15% PA6.6/85% TC) 60b - 38.8 | 1 | 7.15 | 12.05 |
| B2 S-2 (15% PA6.6/85% TC) 80b - 38.4 | 1 | 5.58 | 8.05 |
| B2 S-2 (15% PA6.6/85% TC) 100b - 35.7 | 1 | 5.78 | 9.29 |
| B3 S-2 (70% TC/20% bl/10% pp) 60b - 36.7 | 1 | 5.92 | 12.41 |
| B3 S-2 (70% TC/20% bl/10% pp) 80b - 37.3 | 1 | 7.58 | 13.21 |
| B3 S-2 (70% TC/20% bl/10% pp) 100b - 39.4 | 1 | 6.42 | 10.18 |
| B4 S-2 (30% TC/50% bl/20% pp) 60b - 39.0 | 1 | 6.34 | 12.99 |
| B4 S-2 (30% TC/50% bl/20% pp) 80b - 37.4 | 1 | 6.17 | 10.94 |
| B4 S-2 (30% TC/50% bl/20% pp) 60b - 38.6 | 1 | 5.85 | 9.48 |
| B5 S-2 (85% TC/15% bl/0% pp) 60b - 35.3 | 1 | 5.53 | 12.51 |
| B5 S-2 (85% TC/15% bl/0% pp) 80b - 35.5 | 1 | 7.64 | 11.75 |

Lee White Clotting Assay Assessment of Sample B2, B5S3, and B6 with and without Pectin/Kaolin formulation applied. Six separate experiments are listed. B2: 30TC/50BL/20PP; B6: 100 BL,. B5S3: 33.3% PA6.6, 33.3% TC, 33.3% bl. Positive control is (CG). The Assay is used to assess the ability of the samples to initiate clotting in platelet fresh whole blood by optically assessing clotting rates for fabric treated blood versus untreated blood. Procedure to prepare blood hour preceding assay: Collect swine blood (330 mL) into 35 mL of citrate phosphate dextrose adenine (CPDA-1): 0.327 g/100 mL Citric acid monohydrate. 2.63 g/100 mL Sodium citrate dihydrate. 0.222 g/100 mL Sodium biphosphate monohydrate. 3.195 g/100 mL Dextrose monohydrate. 0.0275 g/100 mL adenine. Pilot: A pilot was run to determine the amount of CaCL required to initiate clotting. 2.5 mL blood was added to a tube containing no fabric or treatment. It was concluded that 5 tnM CaCN should be used based on standard observations of expectation concerning duration to normal clotting with and without fabric. NOTE: 2.5 mL of blood is added to each tube containing the fabric sample. To test the effect of the fabric on whole blood clotting approximately 45-60 seconds transpire between adding CaC12 to the first and last tubes. Tubes were inverted upon addition of CaC12. After all tubes received $CaCl_2$, tubes were placed at 37° C. Reults from a total of 5 separate tests are shown below. Each separate test contained up to 10 tested fabric samples. Treated samples contained different ratios of pectin:kaolin or in some cases a sample was treated with pectin only i.e. sample B2, and untreated samples consisted of the untreated fabric sample without a pectin:kaolin formulation added.

TABLE 7

Comparison of clotting times for whole material samples
Results of Lee White Clotting using freshly collected blood, and testing 5-7 milligram pieces of the above listed materials:

Test #1 (2.5 mL of blood was added to each tube. Started adding CaCl2 to 5 mM with Tube #1 and began timer after all have received $CaCl_2$). Column numbers are in units of minutes.

| | C3:D3 Sample & Pectin:Kaolin Ratio | mm or mg sample | 1 min | 2 | 3 | 4 | 4.5 | 5 | 5.5 | 6 | 6.5 | 7 | 7.5 | 8 | 9 |
|---|---|---|---|---|---|---|---|---|---|---|---|---|---|---|---|
| 1 | B2 Untreated | 12 | | | | | | | | + | + | + | | | |
| 2 | B2 Pectin | | | | | | | | | +/- | + | | | | |
| 3 | B2 Pectin | | | | | | | | | | + | | | | |
| 4 | B2 1:0.5 | | | | | | | + | + | + | + | | | | |
| 5 | B2 1:0.5 | | | | | | | + | + | + | + | | | | |
| 6 | B2 1:0.5 | | | | | | | | + | + | + | | | | |
| 7 | B2 1:1 | | | | | | +/- | + | + | + | + | | | | |
| 8 | B2 1:1 | | | | | | | + | + | + | + | | | | |
| 9 | B2 1:1 | | | | | | | + | + | + | + | | | | |
| 10 | CG | | | | | | + | + | + | + | + | | | | |

Test #2 Started adding CaCl2 to 5 mM with Tube #1 and began timer after all have received $CaCl_2$)

| | D4:E4 | mm | 1 | 2 | 3 | 3.5 | 4 | 4.5 | 5 | 5.5 | 6 | 6.5 | 7 | 7.5 | 8 | 9 |
|---|---|---|---|---|---|---|---|---|---|---|---|---|---|---|---|---|---|
| 1 | B2 1:2.5 | 12 | | | | | | + | | | | | | | | |
| 2 | B2 1:2.5 | | | | | | | + | | | | | | | | |
| 3 | B2 1:2.5 | | | | | | | + | | | | | | | | |
| 4 | B2 1:5 | | | | | | | + | | | | | | | | |
| 5 | B2 1:5 | | | | | | | + | | | | | | | | |
| 6 | B2 1:5 | | | | | | | + | | | | | | | | |
| 7 | B2 1:10 | | | | | | | + | | | | | | | | |
| 8 | B2 1:10 | | | | | | | + | | | | | | | | |
| 9 | B2 1:10 | | | | | | | + | | | | | | | | |
| 10 | CG | | | | | | + | + | | | | | | | | |

Test #1 (Started adding CaCl2 to 5 mM with Tube #1 and began timer after all have received $CaCl_2$)

| | | mm | 1 | 2 | 3 | 4 | 4.5 | 5 | 5.5 | 6 | 6.5 | 7 | 7.5 | 8 | 9 | 10 |
|---|---|---|---|---|---|---|---|---|---|---|---|---|---|---|---|---|---|
| 1 | B2 Untreat | | − | − | + | | | | | | | | | | | | |
| 2 | B2 Pectin | 12 | − | − | − | − | | + | | | | | | | | | |
| 3 | B2 Pectin | 2 × 8 | − | − | + | | | | | | | | | | | | |
| 4 | B2 1:2.5 | 12 | − | + | + | | | | | | | | | | | | |
| 5 | B2 1:2.5 | 2 × 8 | − | − | + | | | | | | | | | | | | |
| 6 | B2 1:2.5 | 2 × 8 | − | + | + | | | | | | | | | | | | |
| 7 | B2 1:5 | 12 | − | + | + | | | | | | | | | | | | |
| 8 | B2 1:5 | 2 × 8 | − | − | + | | | | | | | | | | | | |

TABLE 7-continued

Comparison of clotting times for whole material samples
Results of Lee White Clotting using freshly collected blood, and testing 5-7 milligram pieces of the above listed materials:

| | | | | | | | | | | | | | | |
|---|---|---|---|---|---|---|---|---|---|---|---|---|---|---|
| 9 B2 1:5 | 2 × 8 | − | − | + | | | | | | | | | | |
| 10 CG | 5 mg | − | − | + | | | | | | | | | | |

Test #3 (Started adding CaCl2 with Tube #1 and began timer after all have received CaCl$_2$)

| | mm | 1 | 2 | 3 | 3.5 | 4 | 4.5 | 5 | 5.5 | 6 | 6.5 | 7 | 7.5 | 8 | 9 |
|---|---|---|---|---|---|---|---|---|---|---|---|---|---|---|---|
| 1 B2 1:10 | 12 | − | + | + | + | | + | | | | | | | | |
| 2 B2 1:10 | 2 × 8 | − | + | + | + | | + | | | | | | | | |
| 3 B2 1:10 | 2 × 8 | − | + | + | + | | + | | | | | | | | |
| 4 B5S3 Untreated | 12 | − | − | − | − | | − | | +/− | + | | | | | |
| 5 B5S3 Pectin | 12 | − | − | − | − | | + | | | | | | | | |
| 6 B5S3 1:2.5 | 12 | − | − | + | + | | + | | | | | | | | |
| 7 B5S3 1:2.5 | 2 × 8 | − | − | +/− | + | | + | | | | | | | | |
| 8 B5S3 1:2.5 | 2 × 8 | − | − | + | + | | + | | | | | | | | |
| 9 B5S3 1:5 | 12 | − | − | + | + | | + | | | | | | | | |
| 10 CG | 5 mg | − | − | + | + | | + | | | | | | | | |

Test #4 (Started adding CaCl2 with Tube #1 and began timer after all have received CaCl$_2$)

| | mm | 1 | 2 | 3 | 4 | 4.5 | 5 | 5.5 | 6 | 6.5 | 7 | 7.5 | 8 | 9 |
|---|---|---|---|---|---|---|---|---|---|---|---|---|---|---|
| 1 B5S3 1:5 | 2 × 8 | − | − | + | | + | | + | + | | | | | |
| 2 B5S3 1:5 | 2 × 8 | − | − | + | | + | | + | + | | | | | |
| 3 B5S3 1:10 | 12 | − | − | + | | + | | + | + | | | | | |
| 4 B5S3 1:10 | 2 × 8 | − | − | + | | + | | + | + | | | | | |
| 5 B5S3 1:10 | 2 × 8 | − | − | + | | + | | + | + | | | | | |
| 6 B6 Untreated | 12 | − | − | − | | − | | +/− | + | | | | | |
| 7 B6 Pectin | 12 | − | − | − | | + | | + | + | | | | | |
| 8 B6 1:2.5 | 12 | − | − | + | | + | | + | + | | | | | |
| 9 B6 1:2.5 | 2 × 8 | − | − | + | | + | | + | + | | | | | |
| 10 CG | 5 mg | − | − | + | | + | | + | + | | | | | |

Test #5 (Started adding CaCl2 with Tube #1 and began timer after all have received CaCl$_2$)

| | mm | 1 | 2 | 3 | 3.5 | 4 | 4.5 | 5 | 5.5 | 6 | 6.5 | 7 | 7.5 | 8 | 9 |
|---|---|---|---|---|---|---|---|---|---|---|---|---|---|---|---|
| 1 B6 1:2.5 | 2 × 8 | − | − | + | | | + | | | | | | | | |
| 2 B6 1:5 | 12 | − | − | + | | | + | | | | | | | | |
| 3 B6 1:5 | 2 × 8 | − | − | + | | | + | | | | | | | | |
| 4 B6 1:5 | 2 × 8 | − | − | + | | | + | | | | | | | | |
| 5 B6 1:10 | 12 | − | − | + | | | + | | | | | | | | |
| 6 B6 1:10 | 2 × 8 | − | − | + | | | + | | | | | | | | |
| 7 B6 1:10 | 2 × 8 | − | − | − | | | + | | | | | | | | |
| 8 CG | 5 mg | − | − | + | | | + | | | | | | | | |
| 9 | | | | | | | | | | | | | | | |

TABLE 8a

TEG Results of Pectin/Kaolin (P/K) Formulations Applied to B2 and B6 1:X = Material:

| Sample | R min | stdev | k min | stdev | Angle deg | stdev | MA mm | stdev |
|---|---|---|---|---|---|---|---|---|
| bovine blood - 7376 | 14.7 | 0.8 | 6.1 | 0.9 | 30 | 2.7 | 48.6 | 2.3 |
| B2-UT | 11.4 | 0.5 | 5.6 | 0.3 | 26.8 | 0.8 | 47.8 | 1.9 |
| B2-P | 8.4 | 0.1 | 5.6 | 0.4 | 32.5 | 0.8 | 46.5 | 2.5 |
| B2-1:1-P/K | 3.9 | 0.1 | 2.2 | 0.1 | 49.6 | 11.8 | 46.4 | 1.6 |
| B2-1:2.5-P/K | 3.4 | 0.0 | 2.2 | 0.5 | 65.4 | 1.3 | 45.9 | 2.1 |
| B2-1:5-P/K | 3.4 | 0.4 | 3.0 | 1.1 | 66.9 | 3.3 | 43.0 | 6.9 |
| B2-1:10-P/K | 3.4 | 0.3 | 3.0 | 0.7 | 64.0 | 5.4 | 40.1 | 4.5 |
| B2-1:0.5-P:/ | 4.3 | 0.1 | 3.2 | 0.3 | 53.7 | 2.2 | 41.1 | 1.2 |
| Combat Gauze | 3.5 | 0.3 | 2.5 | 0.3 | 61.8 | 5.1 | 42.0 | 1.9 |
| Bovine Blood - 7419 | 14.3 | 1.9 | 6.4 | 2.0 | 28.4 | 11.5 | 46.3 | 2.8 |
| B6-UT | 10.1 | 1.1 | 7.9 | 0.2 | 21.8 | 2.8 | 45.5 | 1.3 |
| B6-P | 8.5 | 1.1 | 7.5 | 1.7 | 26.1 | 3.8 | 46.2 | 1.4 |
| B6-1:0.5-P/K | 5.0 | 0.4 | 4.8 | 1.5 | 34.7 | 13.3 | 41.5 | 3.5 |
| B6-1:1-P/K | 4.8 | 1.0 | 3.8 | 0.8 | 49.2 | 4.6 | 44.3 | 3.8 |
| B6-1:2.5-P/K | 5.1 | 0.4 | 5.4 | 1.0 | 41.9 | 11.3 | 39.5 | 2.1 |
| B6-1:5-P/K | 4.0 | 0.3 | 4.2 | 1.5 | 44.6 | 10.3 | 41.6 | 2.5 |
| B6-1:10-P/K | 3.6 | 0.5 | 2.2 | 0.6 | 52.2 | 8.5 | 45.6 | 0.7 |
| Combat Gauze | 3.7 | 0.5 | 1.8 | 0.5 | 47.8 | 4.9 | 47.4 | 0.9 |
| Bovine Blood | 14.0 | 2.5 | 6.8 | 3.3 | 26.4 | 19.0 | 43.4 | 1.4 |

B2: 30TC/50BL/20PP
B6: 100 BL

TABLE 8b

| Sample | | R | St Dev | k | St Dev | Angle | St Dev | MA | St Dev |
|---|---|---|---|---|---|---|---|---|---|
| UTF 1H* 85 TC 15 Tencel | Dec. 4, 2015 | 6.5 | 0.4 | 3.2 | 0.1 | 34.1 | 0.8 | 44.2 | 0.8 |
| bovine blood | Dec. 22, 2015 | 16.8 | 1.4 | 6.4 | 0.6 | 22 | 8.3 | 35.8 | 4.5 |
| UT F 1H Pectin and kaolin | Dec. 22, 2015 | 7 | 0.9 | 3.4 | 1.7 | 36.5 | 15.7 | 33.6 | 1.2 |
| bovine blood | Feb. 3, 2016 | 11.8 | 0.4 | 7 | 0.7 | 23.4 | 6.4 | 51.1 | 0.6 |
| B10 (50T/50pp) 60 b-65* | Feb. 3, 2016 | 6 | 1.1 | 5.9 | 1.3 | 25.2 | 3 | 48.6 | 3 |
| 10 mg CaO | Mar. 8-9, 2016 | 3.2 | 0.4 | 3.7 | 0.5 | 47.6 | 3.1 | 90.9* | 2.5 |
| 20 mg CaSiO$_3$ | Mar. 9, 2016 | 9.4 | 2 | 9.3 | 3.5 | 23.9 | 11 | 46.4 | 1.7 |
| 20 mg Al$_2$O$_3$ | Apr. 7, 2016 | 16.4 | 2.3 | 14 | 3.3 | 14.2 | 2.5 | 38.8 | 2.2 |
| 10 mg silica, Ti-doped | | 4.7 | 0.6 | 4.2 | 0.2 | 39.7 | 1.6 | 61.5 | 2.6 |
| blood bovine (B-B6063) | Apr. 20, 2016 | 11.8 | 0.6 | 5.6 | 0.4 | 35.1 | 0 | 62.2 | 2 |
| B7 (100TC/0bl/0pp) 80 b - 36.6* | Apr. 19, 2015 | 7.6 | 0.6 | 3.6 | 0.4 | 38.9 | 9.9 | 66.2 | 3.9 |
| bovine blood (B - B6063) | Apr. 21, 2016 | 13.8 | 0.4 | 5 | 0.3 | 32.6 | 3.5 | 62.4 | 1 |
| B1 (85TC/15bl/0pp) 60 b - 41.9 | Apr. 21, 2016 | 6.8 | 0.4 | 5.8 | 0.4 | 27.4 | 1.9 | 57.6 | 7.9 |
| B2 (30TC/50bl/20pp) 100 b - 34.0* | Apr. 22, 2016 | 9.3 | 1 | 3.8 | 0.3 | 40.1 | 2.4 | 57.3 | 1.5 |
| bovine, blood | May 18, 2016 | 11.2 | 0 | 3.2 | 0.3 | 49.6 | 3.3 | 65.1 | 0.2 |
| B7-100 b-P&K - 36.6 | May 17, 2016 | 4.7 | 0.1 | 3.8 | 1.4 | 43.9 | 9.5 | 67.3 | 0.2 |
| B6 (0TC/100bl/0pp) 100 b - 27.6 P & K treated | May 20, 2016 | 5.4 | 1.1 | 4.3 | 0.8 | 39.6 | 12.5 | 60 | 6.4 |
| B7 (100TC/0bl/0pp) 100 b - 36.6 P & K treated | May 20, 2016 | 5.4 | 1 | 3.2 | 0.9 | 45.9 | 5.6 | 63 | 0.7 |

TABLE 8b-continued

| Sample | | R | St Dev | k | St Dev | Angle | St Dev | MA | St Dev |
|---|---|---|---|---|---|---|---|---|---|
| blood, bovine | Jun. 6, 2016 | 12.6 | 0.6 | 5.4 | 0.3 | 32.9 | 1.6 | 47.8 | 1.7 |
| B6 (0TC/100bl/0pp) 60 b - 27.6 + P and CaTiO3 (10 mg:10 mg) | Jun. 6, 2016 | 10.3 | 1.3 | 6.3 | 0.7 | 27.2 | 6.1 | 49.2 | 1.5 |
| B7 (100TC/0bl/0pp) 60 b - 36.6 + P and CaTiO3 (10 mg:10 mg) | Jun. 6, 2016 | 9.8 | 0.6 | 4.9 | 0.8 | 29.3 | 7.6 | 49.5 | 2.5 |
| 100% TC-60 b-35 + Pectin and TiO2 (10 mg:10 mg) | Jun. 6, 2016 | 9.7 | 0.4 | 5.4 | 0.3 | 33.2 | 3.5 | 48 | 1.1 |
| blood, bovine | Jun. 7, 2016 | 12 | 1.5 | 5.6 | 0.6 | 30.6 | 0.8 | 47 | 0.1 |
| 100% TC-60 b-35 + (Pectin & CaTiO3 10:100 mg) | Jun. 7, 2016 | 8.4 | 0.4 | 4.8 | 0.6 | 32 | 4.2 | 43.8 | 5.2 |
| 100% TC-60 b-35 + Pectin only (10:10 mg/ml) | Jun. 7, 2016 | 8.4 | 0.8 | 5.4 | 0.1 | 22 | 1.1 | 45.7 | 2.7 |
| blood, bovine | Jun. 10, 2016 | 11.7 | 2.3 | 5.9 | 0.6 | 28.6 | 0.7 | 38.6 | 2.4 |
| B7 (100% TC) 60 b - 36.6 + Pectin and CaTiO3 (10:100 mg) | Jun. 10, 2016 | 8.1 | 0.3 | 4.5 | 0.3 | 31.2 | 10.3 | 39.4 | 6.8 |
| blood, bovine | Jun. 17, 2016 | 16.6 | 0.6 | 8 | 0.4 | 26.3 | 1.3 | 48.4 | 2.1 |
| B2 S-2 (15PA6.6/85TC) 60 b - 38.8* | Jun. 17, 2016 | 9.2 | 1.5 | 6.1 | 1.2 | 31.4 | 4.1 | 49.2 | 0.1 |
| blood, bovine | Jul. 11, 2016 | 12.3 | 0.7 | 4.4 | 0.1 | 35.4 | 7.7 | 39.2 | 0.9 |
| B4 S-2 (30% TC, 50% bl/20% pp) 60 b - 39.0 | Jul. 12, 2016 | 11.9 | 1.2 | 6.7 | 2.5 | 20.9 | 1.6 | 37.3 | 1.6 |
| blood, bovine | Jul. 14, 2016 | 12.4 | 0.2 | 4.9 | 0.5 | 38.3 | 4.1 | 31.1 | 0.6 |
| B10 S-2 (33TC/33bl/33pp) 60 b - 36.9 | Jul. 14, 2016 | 10.7 | 0.3 | 5.9 | 1.4 | 23.1 | 5.3 | 34.5 | 1.7 |
| blood, bovine | Jul. 15, 2016 | 12.3 | 0.4 | 5.3 | 0.2 | 21.3 | 11.5 | 29.6 | 2.3 |
| B10 S-2 (33TC/33bl/33pp) 100 b - 37.9 | Jul. 15, 2016 | 10.8 | 0.5 | 4.6 | 1.1 | 29.4 | 15.5 | 31.6 | 0.1 |
| blood, bovine | Jul. 20, 2016 | 15 | 1.7 | 7 | 1.7 | 29.8 | 4.7 | 67.4 | 1.7 |
| B1 S-2 (75PA6.6/25TC) 60 b - 38.2* | Jul. 20, 2016 | 10.9 | 0.3 | 6.4 | 0.1 | 33.8 | 0 | 68.6 | 1.1 |
| bovine blood | Dec. 4, 2015 | 9.4 | 0.9 | 4.6 | 0.8 | 35.8 | 4.2 | 34.3 | 3.3 |
| UTF 1H* 85 TC 15 Tencel | Dec. 4, 2015 | 6.5 | 0.4 | 3.2 | 0.1 | 34.1 | 0.8 | 44.2 | 0.8 |
| bovine blood | Dec. 22, 2015 | 16.8 | 1.4 | 6.4 | 0.6 | 22 | 8.3 | 35.8 | 4.5 |
| UT F 1H Pectin and kaolin | Dec. 22, 2015 | 7 | 0.9 | 3.4 | 1.7 | 36.5 | 15.7 | 33.6 | 1.2 |
| bovine blood | Jan. 27, 2016 | 11.8 | 1.9 | 7.6 | 1.5 | 23.2 | 9.3 | 53.5 | 7.5 |
| B6 (0T/100bl/0pp) 60 b - 27.6* | Jan. 27, 2016 | 8 | 0.3 | 4 | 0.8 | 29.4 | 1.3 | 58.2 | 1.8 |
| bovine blood | Feb. 1, 2016 | 14.6 | 0.6 | 5.5 | 0.3 | 29 | 0.8 | 44.2 | 4.5 |
| B8 (0T/80bl/20pp) 80 b - 39.5 | Feb. 1, 2016 | 6.8 | 0.1 | 5.2 | 0.6 | 25.8 | 2.1 | 48.3 | 1.1 |
| bovine, blood | May 18, 2016 | 11.2 | 0 | 3.2 | 0.3 | 49.6 | 3.3 | 65.1 | 0.2 |
| B7-100 b-P&K - 36.6 | May 17, 2016 | 4.7 | 0.1 | 3.8 | 1.4 | 43.9 | 9.5 | 67.3 | 0.2 |
| B6 (0TC/100bl/0pp) 100 b - 27.6 P & K treated | May 20, 2016 | 5.4 | 1.1 | 4.3 | 0.8 | 39.6 | 12.5 | 60 | 6.4 |
| B7 (100TC/0bl/0pp) 100 b - 36.6 | May 20, 2016 | 5.4 | 1 | 3.2 | 0.9 | 45.9 | 5.6 | 63 | 0.7 |
| blood, bovine | Jun. 6, 2016 | 12.6 | 0.6 | 5.4 | 0.3 | 32.9 | 1.6 | 47.8 | 1.7 |
| B6 (0TC/100bl/0pp) 60 b - 27.6 P and CaTiO3 (10 mg:10 mg) | Jun. 6, 2016 | 10.3 | 1.3 | 6.3 | 0.7 | 27.2 | 6.1 | 49.2 | 1.5 |

TABLE 8b-continued

| Sample | | R | St Dev | k | St Dev | Angle | St Dev | MA | St Dev |
|---|---|---|---|---|---|---|---|---|---|
| B7 (100TC/0bl/0pp) 60 b - 36.6 P and CaTiO3 (10 mg:10 mg) | Jun. 6, 2016 | 9.8 | 0.6 | 4.9 | 0.8 | 29.3 | 7.6 | 49.5 | 2.5 |
| 100% TC-60 b-35 Pectin and TiO2 (10 mg:10 mg) | Jun. 6, 2016 | 9.7 | 0.4 | 5.4 | 0.3 | 33.2 | 3.5 | 48 | 1.1 |
| blood, bovine | Jun. 7, 2016 | 12 | 1.5 | 5.6 | 0.6 | 30.6 | 0.8 | 47 | 0.1 |
| 100% TC-60 b-35* | Jun. 7, 2016 | 8.4 | 0.4 | 4.8 | 0.6 | 32 | 4.2 | 43.8 | 5.2 |
| blood, bovine | Jun. 10, 2016 | 11.7 | 2.3 | 5.9 | 0.6 | 28.6 | 0.7 | 38.6 | 2.4 |
| B7 (100% TC) 60 b - 36.6 Pectin and CaTiO3 (10:100 mg) | Jun. 10, 2016 | 8.1 | 0.3 | 4.5 | 0.3 | 31.2 | 10.3 | 39.4 | 6.8 |
| blood, bovine | Jun. 17, 2016 | 16.6 | 0.6 | 8 | 0.4 | 26.3 | 1.3 | 48.4 | 2.1 |
| B2 S-2 (15PA6.6/85TC) 60 b - 38.8* | Jun. 17, 2016 | 9.2 | 1.5 | 6.1 | 1.2 | 31.4 | 4.1 | 49.2 | 0.1 |
| blood, bovine | Jul. 15, 2016 | 12.3 | 0.4 | 5.3 | 0.2 | 21.3 | 11.5 | 29.6 | 2.3 |
| B10 S-2 (33TC/33bl/33pp) 100 b - 37.9* | Jul. 15, 2016 | 10.8 | 0.5 | 4.6 | 1.1 | 29.4 | 15.5 | 31.6 | 0.1 |
| Bovine Blood (B-B6374) | Aug. 2-4, 2016 | 13.4 | 0.8 | 3.6 | 0.4 | 38 | 6.3 | 63.4 | 3.2 |
| B1-S2-60 bar (75% PA6.6/25% TC) | Aug. 3, 2016 | 11 | 0.8 | 3.4 | 0.3 | 44.8 | 3.7 | 62.5 | 2 |

TABLE 9

Description of Layered Samples*

Layers were combined by needle punching and in some cases a needle punch fabric was employed as the outside layer.

| Sample i.d. | Needle punched layer | Hydroentangled layer | Other Information |
|---|---|---|---|
| Sample 1 | | 50BL/50TC + 50TC/50PP | 2 layers |
| Sample 2 | | 80Bl/20TC + 50Bl/50TC | 2 layer |
| Sample 3 | 30TC/50Bl/20PP | 50TC/50PP | 3 layers with VE-4 on the outside |
| Batch 2-1 | 80Bl/20TC | 50PP/50TC | |
| Batch 2-2 | 75TC/25PP | 80Bl/20TC | 2 layers |
| Batch 2-3 | 80Bl/20TC | 50TC/50PP (Thermal) | 2 layers |
| Batch 2-4 | 80Bl/20TC | 50TC/50PP (Bico) | 2 layer |
| Batch 1 | 50PP/50TC | 80Bl/20TC | 3 layers with 80Bl/20TC on outside |
| NP-2 | 50TC/50PP (thermal) | VE-4 on both sides | 3 layers |
| NP-3 | 75TC/25PP | VE-4 on both sides | 3 layers |
| NP-4 | 50TC/50PP (Bico) | VE-4 | 2 layers |
| NP-5 | 75TC/25 PP (Bico) | VE-4 | 2 layers |
| NP-6 | 50TC/50PP | VE-4 | 2 layers |
| NP-7 | | VE-4 + 50TC/50PP | 3 layers VE-4 on both sides which were bonded by way of needle punch. |

VE-4 = 30TC/50Bl/20PP

Bico = refers to bicomponent fiber containing polyethylene and polypropylene

Thermal = refers to blending of fibers using a thermoplastic process that combines the cotton with the polypropylene thermally.

The table describes samples that were combined on the same day in an operation to create layered dressing material. Sample i.d.s correspond with i.d. descriptions in FIG. 9 & FIG. 10, which describe the absorbency and wicking activities of some of the samples.

We claim:

1. A single layered nonwoven fabric comprising about 5% by weight to about 95% by weight non-scoured, non-bleached greige cotton fibers, about 5% by weight to about 95% by weight bleached cotton fibers, and about 5% by weight to about 60% by weight hydrophobic fibers, all percentages adding up to 100 wt %.

2. The single layered nonwoven fabric according to claim 1, wherein said fabric comprises about 60% by weight non-scoured, non-bleached greige cotton fibers, about 20% by weight bleached cotton fibers, and about 20% by weight hydrophobic fibers.

3. The single layered nonwoven fabric according to claim 1, wherein said hydrophobic fibers are selected from the group consisting of polypropylene, nylon, and mixtures thereof.

4. The single layered nonwoven fabric according to claim 1, wherein said non-scoured, non-bleached greige cotton has a purity level of about 99.9%.

5. The single layered nonwoven fabric according to claim 1, wherein said fabric further comprises kaolin and pectin, wherein said pectin adheres said kaolin to said fibers.

6. The single layered nonwoven fabric according to claim 1, wherein said nonwoven fabric is produced by a process comprising:
(a) preparing needle punched webs of the fibers,
(b) uniformly hydroentangling said webs using a system wherein said system is equipped with one low water pressure jet head that wets said webs on the top face of said webs to form a wetted substrate and wherein said system is equipped with two high water pressure jet heads that subsequently alternatively wets said wetted substrate on either face of said wetted substrate, wherein said system utilizes an about 23 mesh to about 17 mesh screen, and
(c) drying said wetted substrate to form said fabric.

7. A single layered nonwoven fabric comprising about 5% by weight to about 95% by weight non-scoured, non-bleached greige cotton fibers, about 5% by weight to about 95% by weight bleached cotton fibers, and about 5% by weight to about 60% by weight hydrophobic fibers, all percentages adding up to 100 wt %, wherein said nonwoven fabric is produced by a process comprising:
(a) preparing needle punched webs of the fibers,
(b) uniformly hydroentangling said webs using a system wherein said system is equipped with one low water pressure jet head that wets said webs on the top face of said webs to form a wetted substrate and wherein said system is equipped with two high water pressure jet heads that subsequently alternatively wets said wetted substrate on either face of said wetted substrate, wherein said system utilizes an about 23 mesh to about 17 mesh screen, and
(c) drying said wetted substrate to form said fabric.

8. A multi-layered nonwoven wound dressing, comprising at least one inner layer containing about 50% by weight to about 95% by weight non-scoured, non-bleached greige cotton fibers and about 5% by weight to about 50% by weight hydrophobic fibers, all percentages adding up to 100 wt %, and at least one outer layer containing about 5% by weight to about 95% by weight non-scoured, non-bleached greige cotton fibers, about 5% by weight to about 95% by weight bleached cotton fibers, and about 5% by weight to about 60% by weight hydrophobic fibers, all percentages adding up to 100 wt %.

9. The single layered nonwoven fabric of claim 1, wherein the fabric has a density higher than about 30 g/m$^2$.

10. The single layered nonwoven fabric of claim 1, wherein the fabric has an increased absorption capacity of about 60% to about 70% when compared with a fabric not comprising non-scoured, non-bleached greige cotton fibers.

11. The single layered nonwoven fabric of claim 1, further comprising ascorbic acid or sodium ascorbate.

12. The single layered nonwoven fabric of claim 11, wherein the fabric comprises about 10 mM ascorbic acid or sodium ascorbate.

13. A single layered nonwoven fabric comprising about 5% by weight to about 95% by weight non-scoured, non-bleached greige cotton fibers, and about 5% by weight to about 95% by weight bleached cotton fibers, all percentages adding up to 100 wt %.

14. The single layered nonwoven fabric according to claim 13, wherein said fabric comprises about 85% by weight non-scoured, non-bleached greige cotton fibers, and about 15% by weight bleached cotton fibers.

15. A wound dressing comprising the single-layered nonwoven fabric of claim 1.

16. A wound dressing comprising the single-layered nonwoven fabric of claim 2.

17. A wound dressing comprising the single layered nonwoven fabric of claim 13.

* * * * * ns
EX PARTE REEXAMINATION CERTIFICATE (12581st)

United States Patent
Edwards et al.

(10) Number: US 11,246,756 C1
(45) Certificate Issued: Apr. 18, 2024

(54) HEALTHCARE TEXTILES

(71) Applicants: The United States of America, as Represented by the Secretary of Agriculture, Washington, DC (US); H&H Medical Inc., Bena, VA (US); TJ Beall, Greenwood, MS (US)

(72) Inventors: Judson V. Edwards, Mandeville, LA (US); Joseph Dacorta, Bena, VA (US); Gary Lawson, Greenwood, MS (US)

(73) Assignee: H & H MEDICAL CORPORATION, Williamsburg, VA (US)

Reexamination Request:
No. 90/019,298, Nov. 17, 2023

Reexamination Certificate for:
Patent No.: 11,246,756
Issued: Feb. 15, 2022
Appl. No.: 16/110,169
Filed: Aug. 23, 2018

(51) Int. Cl.
| | |
|---|---|
| *A61F 13/01* | (2024.01) |
| *A61F 13/00* | (2024.01) |
| *A61F 13/511* | (2006.01) |
| *A61L 15/24* | (2006.01) |
| *A61L 15/28* | (2006.01) |
| *A61L 15/40* | (2006.01) |
| *A61L 15/42* | (2006.01) |
| *A61L 15/44* | (2006.01) |
| *D04H 1/425* | (2012.01) |
| *D04H 1/498* | (2012.01) |

(52) U.S. Cl.
CPC .. *A61F 13/01012* (2024.01); *A61F 13/51113* (2013.01); *A61F 13/51121* (2013.01); *A61L 15/24* (2013.01); *A61L 15/28* (2013.01); *A61L 15/425* (2013.01); *A61L 15/44* (2013.01); *D04H 1/425* (2013.01); *A61F 2013/00106* (2013.01); *A61F 2013/00217* (2013.01); *A61F 2013/00319* (2013.01); *A61F 2013/0054* (2013.01); *A61F 2013/00736* (2013.01); *A61F 2013/00744* (2013.01); *A61F 2013/00748* (2013.01); *A61L 15/40* (2013.01); *D04H 1/498* (2013.01)

(58) Field of Classification Search
CPC ........ B32B 2262/062; B32B 2264/062; B32B 2317/10; D10B 2201/02; D04H 1/02; D04H 1/425; D04H 1/498; A61F 13/01012; A61F 13/51113; A61F 13/51121; A61F 2013/00106; A61F 2013/00217; A61F 2013/00319; A61F 2013/0054; A61F 2013/00736; A61F 2013/00744; A61F 2013/00748; A61L 15/24; A61L 15/28; A61L 15/425; A61L 15/44; A61L 15/40
See application file for complete search history.

(56) References Cited

To view the complete listing of prior art documents cited during the proceeding for Reexamination Control Number 90/019,298, please refer to the USPTO's Patent Electronic System.

*Primary Examiner* — Norca L. Torres Velazquez

(57) ABSTRACT

Single layered nonwoven wound dressings containing (1) about 5% by weight to about 95% by weight (e.g., 5% to 95%) non-scoured, non-bleached greige cotton fibers, (2) about 5% by weight to about 95% by weight (e.g., 5% to 95%) bleached cotton fibers, and (3) about 5% by weight to about 60% by weight (e.g., 5% to 60%) hydrophobic fibers (e.g., polypropylene, nylon); all percentages adding up to 100 wt %. Also, multi-layered nonwoven wound dressings, containing (1) at least one inner layer containing (a) about 50% by weight to about 95% by weight (e.g., 50% to 95) non-scoured, non-bleached greige cotton fibers and (b) about 5% by weight to about 50% by weight (e.g., 5% to 50%) hydrophobic fibers, all percentages adding up to 100 wt %, and (2) at least one outer layer containing (a) about 5% by weight to about 95% by weight (e.g., 5% to 95%) non-scoured, non-bleached greige cotton fibers, (b) about 5% by weight to about 95% by weight (e.g., 5% to 95%) bleached cotton fibers, and (c) about 5% by weight to about 60% by weight (e.g., 5% to 60%) hydrophobic fibers (e.g., polypropylene, nylon); all percentages adding up to 100 wt %.

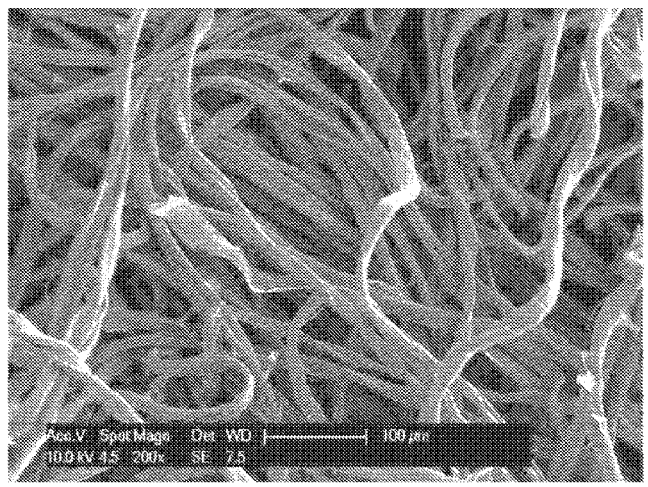

EX PARTE REEXAMINATION CERTIFICATE

NO AMENDMENTS HAVE BEEN MADE TO THE PATENT

AS A RESULT OF REEXAMINATION, IT HAS BEEN DETERMINED THAT:

The patentability of claims 1 and 13 is confirmed.

Claims 2-12 and 14-17 were not reexamined.

\* \* \* \* \*